United States Patent [19]
Warner et al.

[11] Patent Number: 5,383,889
[45] Date of Patent: Jan. 24, 1995

[54] TETHERED EVERTING BALLOON RETRACTOR FOR HOLLOW BODIES AND METHOD OF USING

[75] Inventors: Robert D. Warner, Cupertino; Albert K. Chin; Gail Stevens, both of Palo Alto, all of Calif.

[73] Assignee: Origin Medsystems, Inc., Menlo Park, Calif.

[21] Appl. No.: 959,259

[22] Filed: Oct. 9, 1992

Related U.S. Application Data

[63] Continuation-in-part of Ser. No. 890,941, May 29, 1992, which is a continuation-in-part of Ser. No. 762,318, Sep. 19, 1991, which is a continuation-in-part of Ser. No. 706,781, May 29, 1991, abandoned.

[51] Int. Cl.$^6$ ............................................. A61M 29/02
[52] U.S. Cl. ........................................ 606/192; 604/96
[58] Field of Search .................. 604/96; 606/192, 193, 606/194; 128/898

[56] References Cited

U.S. PATENT DOCUMENTS

| | | | |
|---|---|---|---|
| 3,168,092 | 2/1965 | Silverman | 606/192 |
| 4,137,906 | 2/1979 | Akiyama et al. | 606/192 |
| 4,271,839 | 6/1981 | Fogarty et al. | 606/194 |
| 4,318,410 | 3/1982 | Chin | 606/194 |
| 4,493,711 | 1/1985 | Chin et al. | 604/271 |
| 4,863,440 | 9/1989 | Chin | 604/271 |
| 4,966,583 | 10/1990 | Debbas | 604/98 |
| 5,159,925 | 11/1992 | Neuwirth et al. | 128/401 |
| 5,183,463 | 2/1993 | Debbas | 606/192 |
| 5,183,464 | 2/1993 | Dubrul et al. | 128/3 |
| 5,195,959 | 3/1993 | Smith | 604/34 |
| 5,197,948 | 3/1993 | Ghodsian | 604/96 |
| 5,197,971 | 3/1993 | Bonutti | 606/192 |
| 5,201,752 | 4/1993 | Brown et al. | 606/190 |

*Primary Examiner*—Ren Yan
*Attorney, Agent, or Firm*—Limbach & Limbach

[57] ABSTRACT

An apparatus for applying a manipulating force to manipulate a hollow body. The apparatus comprises a hollow shaft at the distal end of which is attached an elastomeric balloon that is inflatable from a collapsed state to an expanded state to engage the hollow body. A tether, attached to the distal tip of the elastomeric balloon, limits distal excursion, and freely allows proximal excursion, of the distal tip of the elastomeric balloon in response to the manipulating force. The tether may be flexible, with its distal end attached to the distal tip of the elastomeric balloon, and its proximal end attached within the hollow shaft. Alternatively, the tether may include an elongate member slidably mounted within the hollow shaft, and a stop that limits distal sliding of the elongate member. The distal tip of the balloon is attached to the distal end of the elongate member. In a method according to the invention for manipulating a hollow body, the apparatus just described is provided. The elastomeric balloon of the apparatus is introduced in a collapsed state into an interior volume of the hollow body. The elastomeric balloon is expanded to its expanded state to occupy at least a major portion of the interior volume of the hollow body. Finally, a manipulating force is applied to the hollow shaft to manipulate the hollow body.

25 Claims, 13 Drawing Sheets

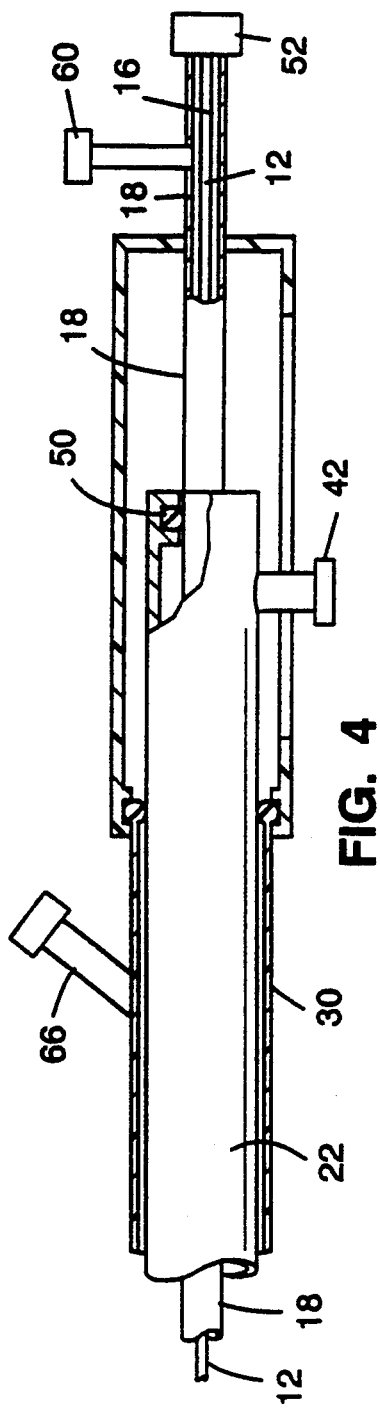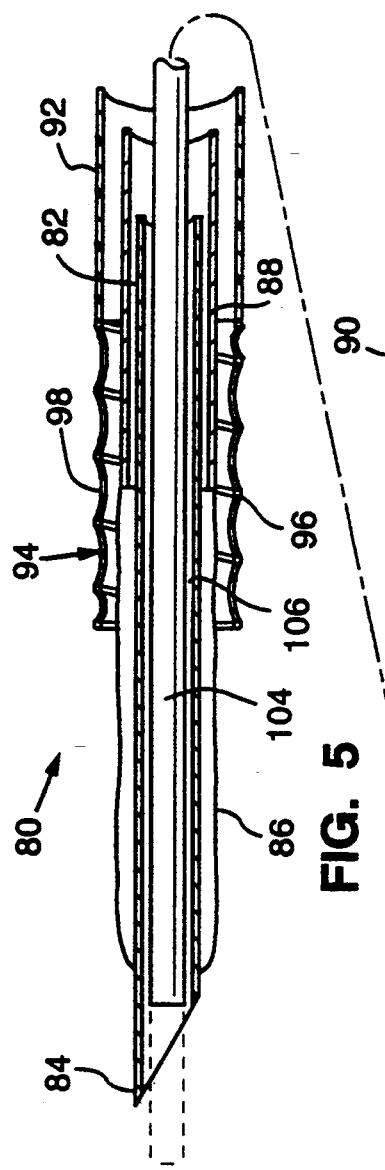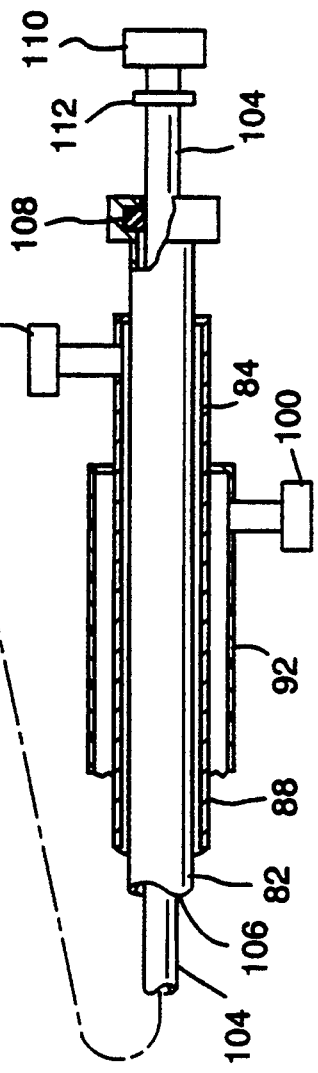

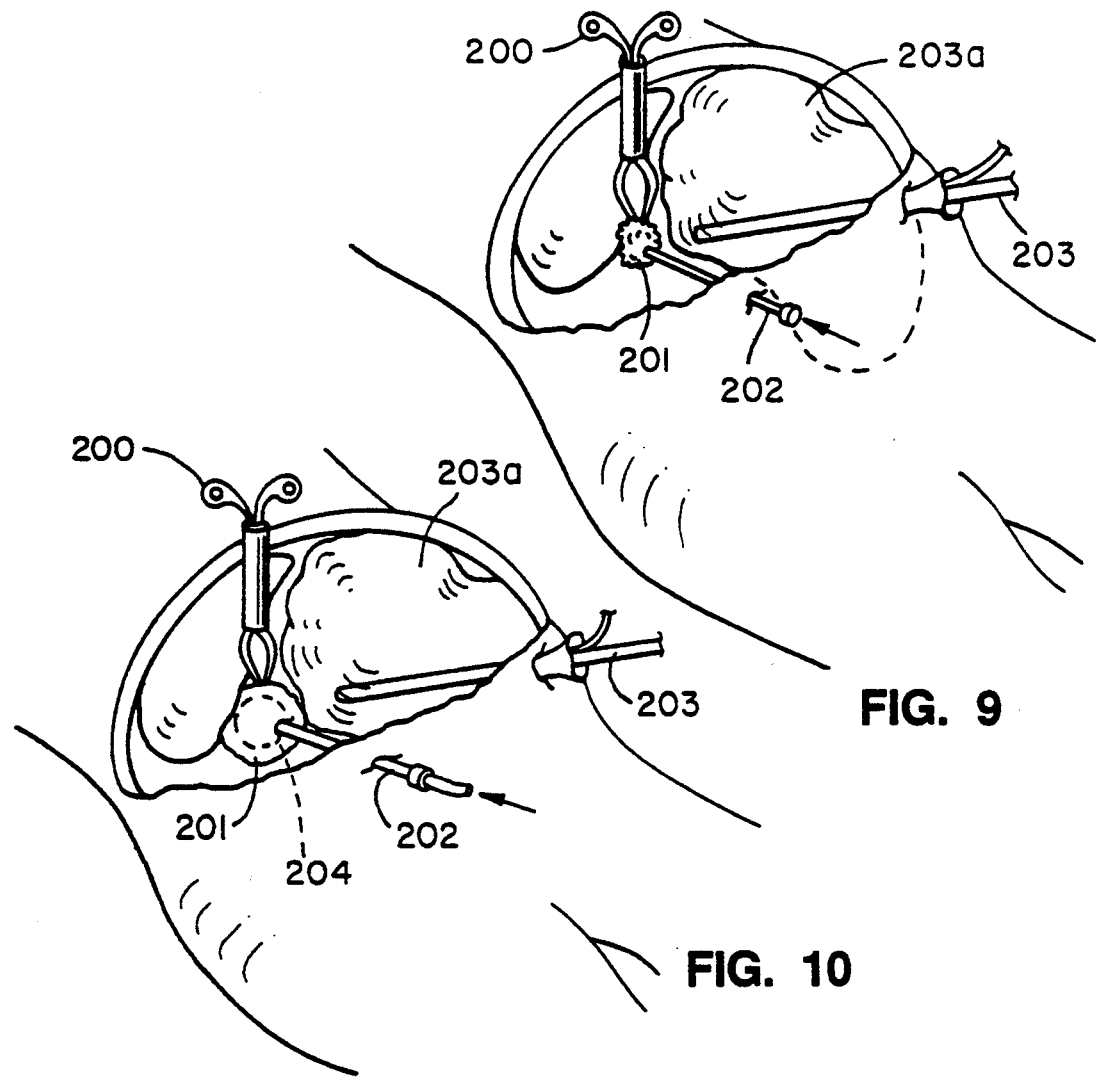
FIG. 9
FIG. 10
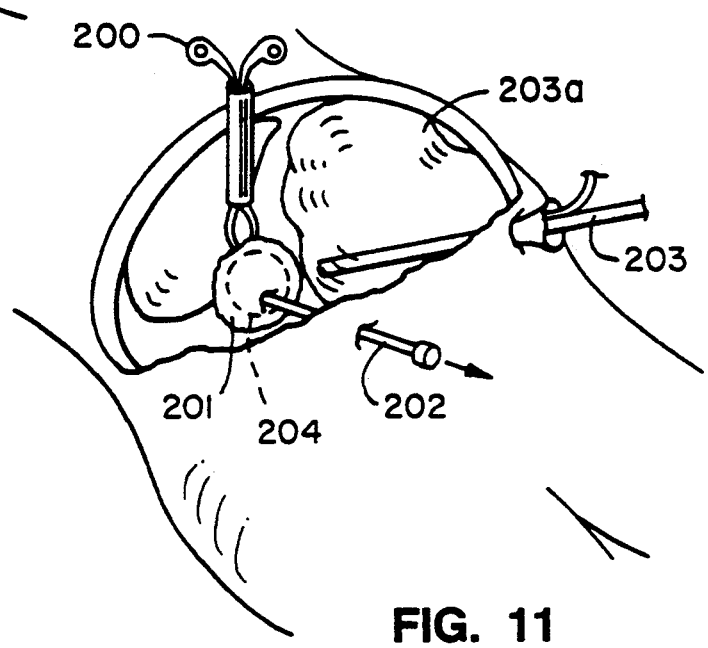
FIG. 11

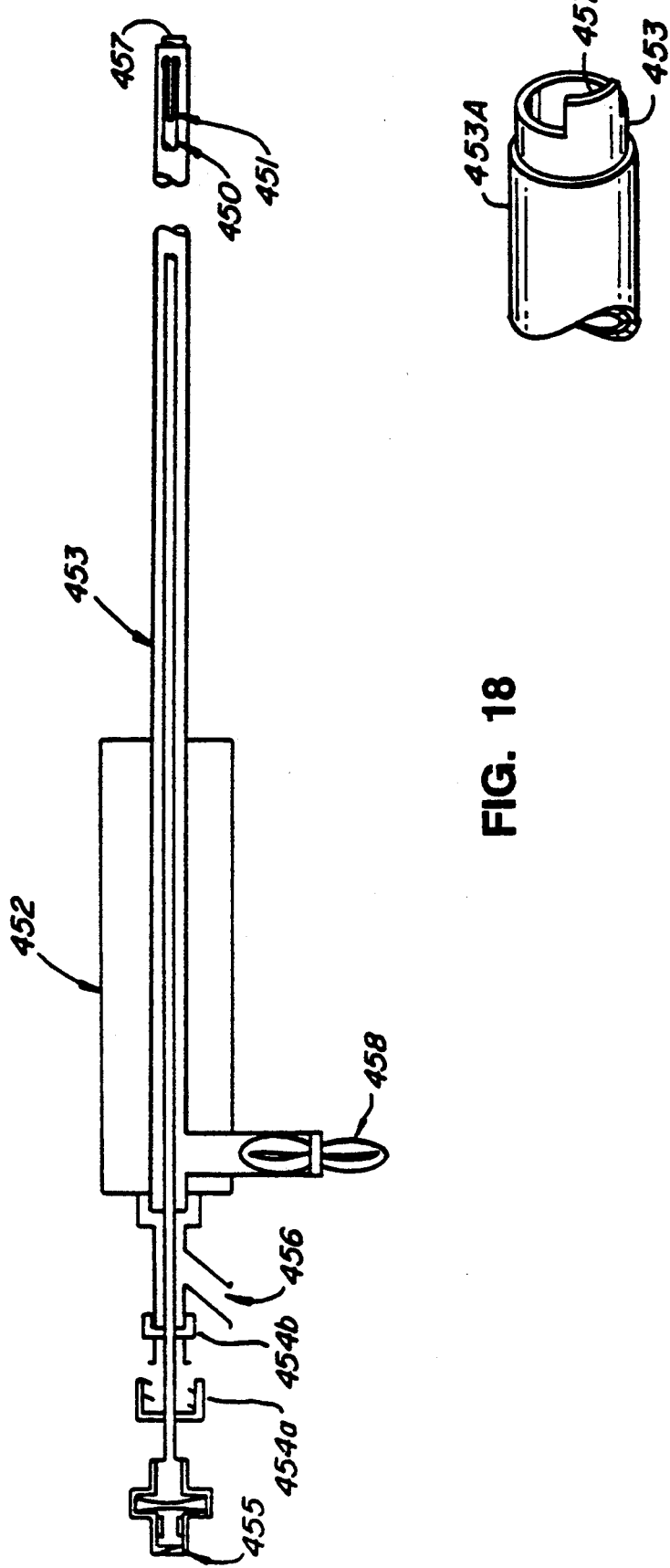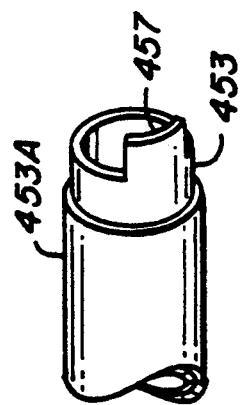
FIG. 18
FIG. 18A

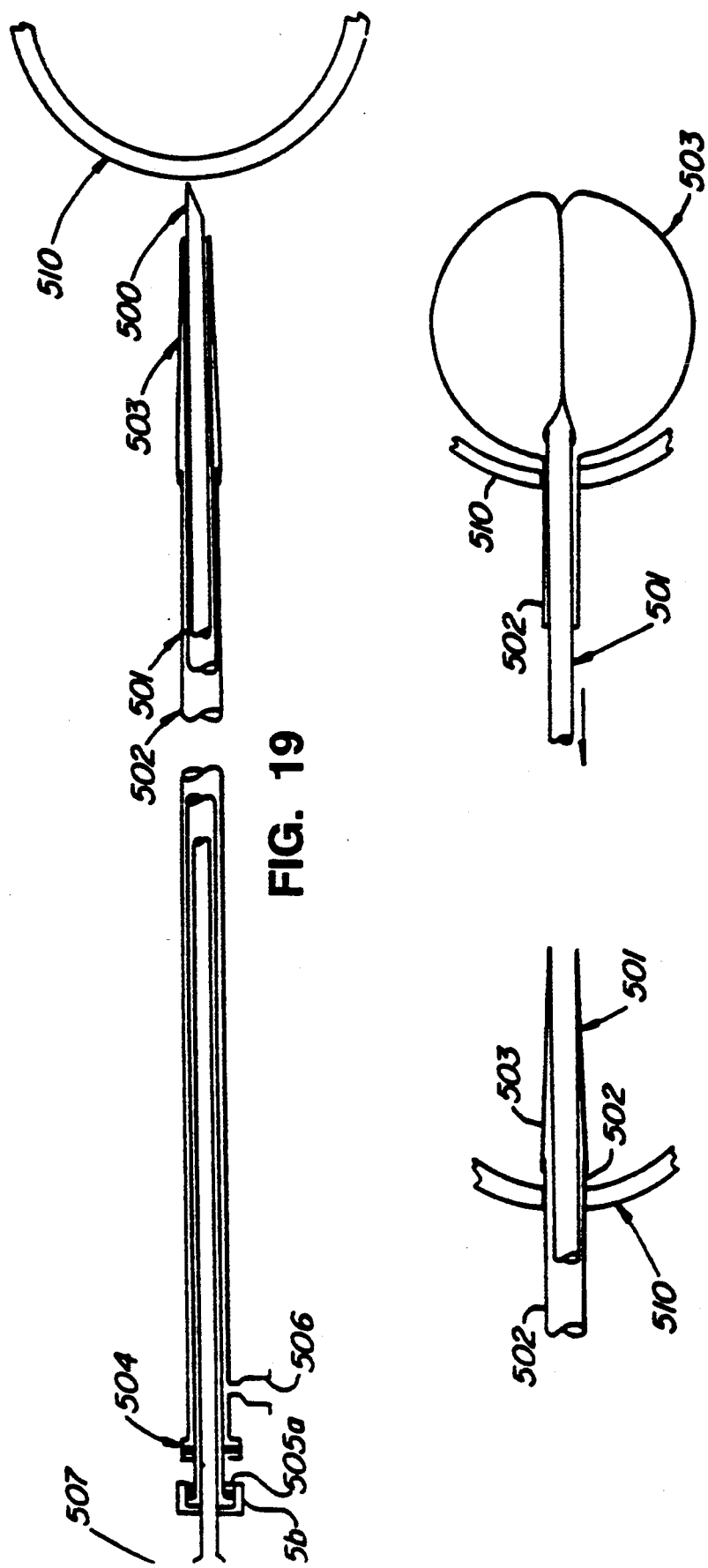

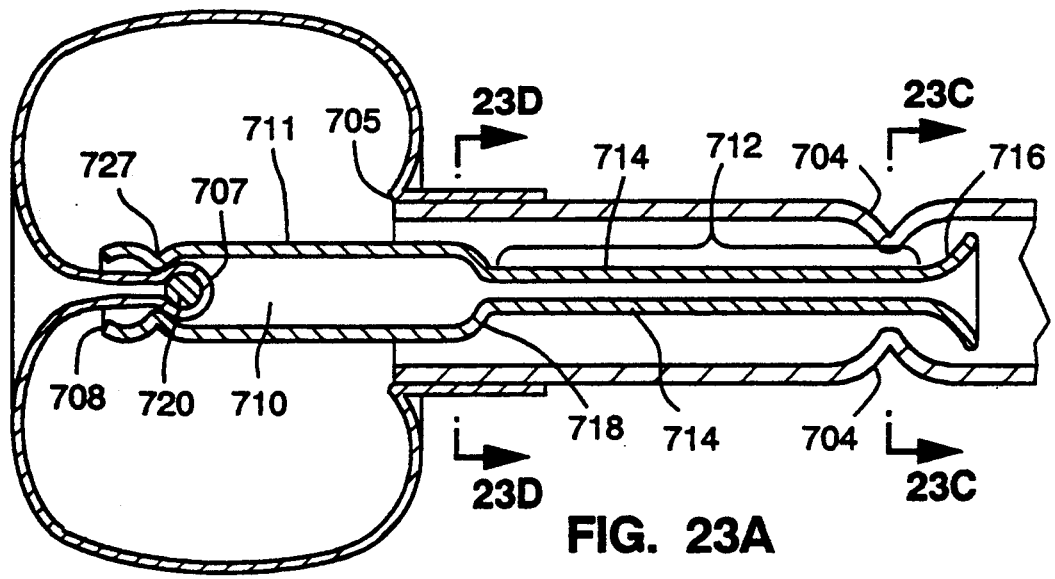
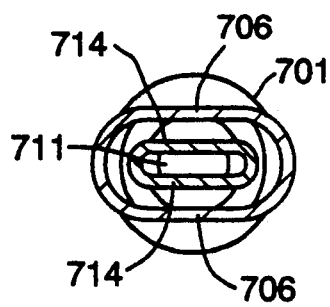
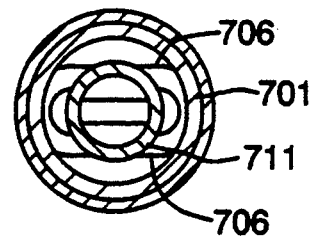
FIG. 23C
FIG. 23D
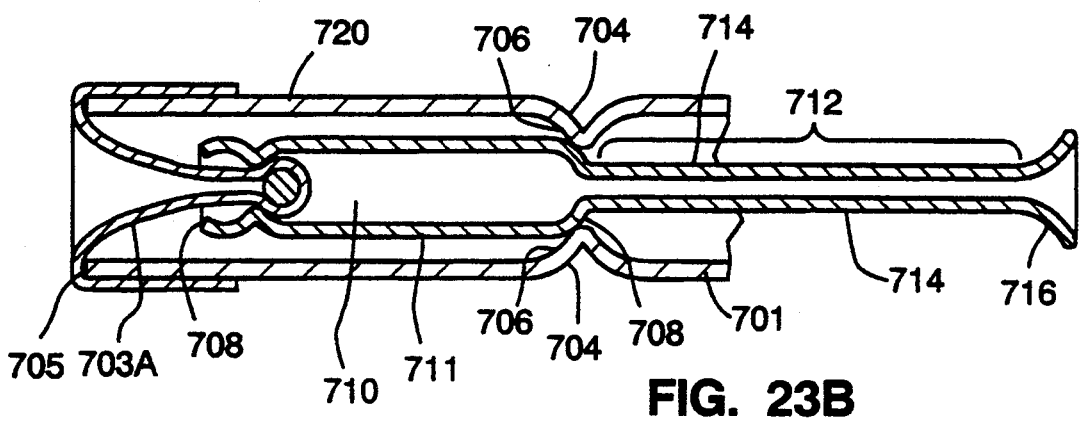
FIG. 23B

TETHERED EVERTING BALLOON RETRACTOR FOR HOLLOW BODIES AND METHOD OF USING

This application is a continuation-in-part of application Ser. No. 07/890,941, filed May 29, 1992, which is a continuation-in-part of application Ser. No. 07/762,318, filed Sep. 19, 1991, which is a continuation-in-part of Ser. No. 07/706,781, filed on May 29, 1991, now abandoned, the full disclosures of which are incorporated herein by reference.

FIELD OF THE INVENTION

The present invention relates generally to the structure and use of surgical instruments, and more particularly to a method and apparatus for manipulating and dissecting body structures during surgical procedures.

BACKGROUND OF THE INVENTION

Minimally invasive surgical (MIS) techniques, such as laparoscopic, endoscopic, and arthroscopic surgery, are generally performed through small incisions using specialized instruments to accomplish the desired surgical procedure. Usually, the instruments are introduced through a narrow-diameter tube, such as a trocar sleeve, while the physician observes manipulation of the instruments through specialized imaging equipment, such laparoscopes, endoscopes, and arthroscopes. Such MIS techniques offer significant advantages over conventional "open" surgical procedures. In particular, the MIS techniques are usually less traumatic, require a shorter recovery time, and are less costly than corresponding conventional surgical procedures.

Of particular interest to the present invention are laparoscopic cholecystectomy procedures where the gallbladder is surgically severed (commonly referred to as dissected) and withdrawn through a small trocar sleeve, typically having a diameter of about 10 mm. In order to manipulate the gallbladder, several grasping forceps are introduced through additional trocar sheaths, and the position of the gallbladder is constantly changed in order to expose the interface between the gallbladder and surrounding tissue, particularly the liver, to permit dissection. The actual dissection has usually been performed using forceps, hooks, and/or a small gauze pledget to tear and tease the gallbladder from the surrounding tissue along the dissection plane.

While laparoscopic cholecystectomy procedures have been very successful and have become increasingly common, the need to simultaneously handle multiple graspers as well as a dissection instrument places great demands on the physician and usually requires coordination with one or more surgical assistants. The difficulty in performing the procedure is exacerbated by the slickness of the gallbladder surface, and overly vigorous attempts to capture the gallbladder can result in perforation, bile spillage, and gallbladder collapse. A collapsed gallbladder is even more difficult to dissect from the surrounding tissue than an intact gallbladder.

The applications of which this application is a continuation-in-part (the "prior applications") describe a number of retractors for manipulating hollow bodies, in particular, for manipulating the gall bladder in the course of performing a laparoscopic cholecystectomy. The retractors described in the prior applications comprise an elastomeric balloon attached to the distal end of a hollow shaft. With the balloon in a collapsed state, the distal end of the hollow shaft is inserted through an entry hole into the hollow body to be manipulated and the balloon is inflated into an expanded state inside the hollow body. The expanded balloon grips the inside of the hollow body and enables the hollow body to be manipulated as required in the course of a surgical procedure. For example, the retractor can be used to manipulate the gall bladder in the course of a laparoscopic cholecystectomy.

Practical experience has shown that a large manipulation force applied to the hollow shaft causes the elastomeric balloon to distend. Part of the balloon pulls back through the entry hole, resulting in reduced control over the body being manipulated. Distention of the balloon can stretch the balloon to its limit, and cause the balloon to rupture. Moreover, when the balloon is distended, the envelope of the balloon forms a relatively shallow angle relative to the entry hole. The balloon then acts as a lever, stretching, and possibly tearing, the entry hole, which allows the balloon to escape from the hollow body. Finally, when the balloon is distended, it becomes incapable of transmitting a manipulating torque to the hollow body, which reduces the number of manipulating motions available to the surgeon.

The prior applications also show retractors in which the balloon is mounted on the hollow shaft with the balloon attached to the hollow shaft at both ends of a diameter of the balloon. Attaching the balloon to the hollow shaft at both ends of a diameter makes the balloon less prone to distention, and thus to rupturing, and makes the balloon less likely to tear the entry hole. However, with this arrangement, the distal end of the rigid hollow shaft remains deep inside the hollow body while the hollow body is manipulated. Consequently, considerable care must be exercised when manipulating the hollow body using this type of retractor, particularly when applying a manipulating force in the distal direction, to prevent the distal end of the hollow shaft from puncturing or otherwise injuring the hollow body.

OBJECTS AND SUMMARY OF THE INVENTION

It is an object of the present invention to provide a retractor for manipulating a hollow body, such as the gall bladder, in which distention of the balloon, and the consequent reduction of control and risk of tearing the entry hole, is avoided when a large manipulation force is applied to the retractor.

It is an object of the present invention to provide a retractor for manipulating a hollow body, such as the gall bladder, in which the risk of injuring the hollow body due to the presence of a non-compliant part of the retractor in the hollow during manipulation is reduced.

It is an object of the present invention to provide a retractor for manipulating a hollow body, such as the gall bladder, which is capable of applying a torque to the hollow body during manipulation.

Accordingly, the invention provides an apparatus for applying a manipulating force to manipulate a hollow body. The apparatus comprises a hollow shaft having an elastomeric balloon attached to its distal end. The elastomeric balloon is inflatable from a collapsed state to an expanded state to engage the hollow body. The apparatus also includes a tether attached to the distal tip of the elastomeric balloon. The tether limits distal excursion of the distal tip of the elastomeric balloon, and freely permits proximal excursion of the distal tip of the elastomeric balloon, in response to the manipulating force.

In a first variation, the tether is flexible and has a distal end attached to the distal tip of the elastomeric balloon, and a proximal end attached within the hollow shaft.

In a second variation, the tether includes an elongate member slidably mounted within the hollow shaft, and a stop that limits distal sliding of the elongate member. The distal tip of the balloon is attached to the distal end of the elongate member.

The invention also provides a method for applying a manipulating force to manipulate a hollow body. In the method according to the invention, a retraction apparatus is provided that has a hollow shaft with an elastomeric balloon attached to its distal end. The elastomeric balloon is inflatable from a collapsed state to an expanded state to engage the hollow body. The retraction apparatus also includes a tether attached to the distal tip of the elastomeric balloon. The tether limits distal excursion of the distal tip of the elastomeric balloon, and freely permits proximal excursion of the distal tip of the elastomeric balloon, in response to the manipulating force. The elastomeric balloon is introduced in the collapsed state into an interior volume of the hollow body. The elastomeric balloon is expanded to the expanded state to occupy at least a major portion of the interior volume. Finally, the manipulating force is applied to the hollow shaft to manipulate the hollow body.

BRIEF DESCRIPTION OF THE DRAWINGS

FIG. 4 illustrates the proximal end of the retractor of FIG. 1, shown in partial section with portions broken away.

FIG. 5 illustrates an alternate embodiment of a retractor in which the elastomeric balloon is attached to the hollow shaft at both ends of a diameter of the balloon, and in which part of the hollow shaft is present in the hollow body during manipulation.

FIGS. 9, 10 and 11 illustrate the method of the invention for manipulating and dissecting the gallbladder in conjunction with an abdominal lifting device to facilitate access.

FIGS. 15, 16, 18, 18A and 19 illustrate embodiments of a retractor having an elastomeric balloon attached to the distal end of a hollow shaft.

FIGS. 19A and 19B illustrate the use of the retractor shown in FIG. 19.

FIGS. 23A and 23B show the preferred embodiment of a retractor according to the invention with the elastomeric balloon in its expanded state and its inverted, collapsed state, respectively.

FIG. 23C shows a cross section of the preferred embodiment of a retractor according to the invention along the line X—X' in FIG. 23A.

FIG. 23D shows a cross section of the preferred embodiment of a retractor according to the invention along the line Y—Y' in FIG. 23A.

DETAILED DESCRIPTION OF THE INVENTION

Figure 1:
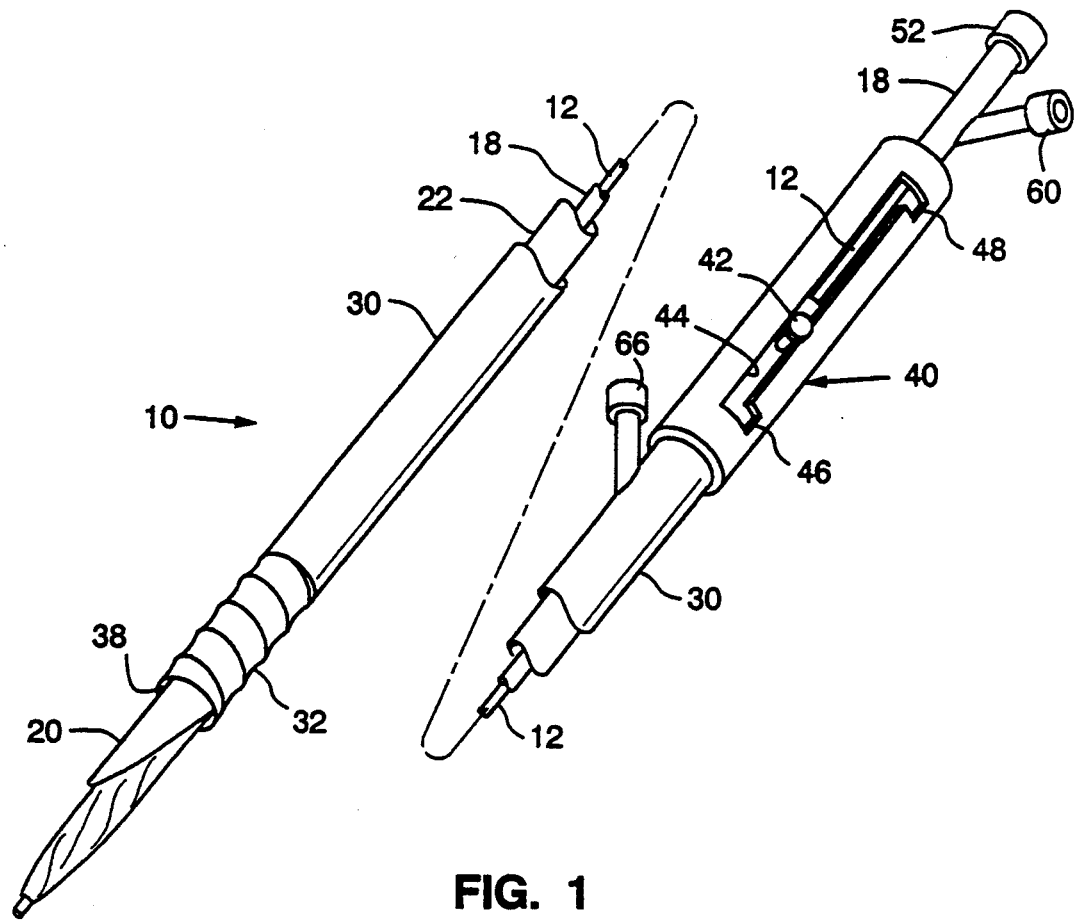
FIG. 1 is a perspective view of a retractor in which the elastomeric balloon is attached to the hollow shaft at both ends of a diameter of the balloon, and in which part of the hollow shaft is present in the hollow body during manipulation.

The method and apparatus of the present invention are useful for manipulating and dissecting a variety of body structures in surgical procedures, particularly minimally invasive surgical (MIS) procedures where the apparatus are introduced through narrow diameter trocar sleeves and manipulated under the control of imaging equipment, as described generally above. While the methods and apparatus are particularly useful for removing the gallbladder during laparoscopic cholecystectomy procedures, as will be described in detail below, and they will also be useful for treating other body organs and structures during other surgical procedures, both MIS and conventional open surgical procedures. For example, the methods and apparatus of the present invention will be useful for the partial or total removal of the stomach in gastrectomy procedures; manipulation of the intestines during bowel resection and other procedures; manipulation of the uterus in hysterectomy procedures; manipulation of a segment of the lung in lung resections; manipulation of pericardial cavity in cardiac diagnostic and therapeutic procedures including endocardial mapping, ablation, and defibrillation electrode placement; and the like. This list of body structures and procedures is not meant to be exhaustive, and the methods and apparatus of the present invention may find a variety of additional uses.

The methods of the present invention rely on introducing an expandable member to the interior volume of a hollow body structure, usually through a penetration formed in the wall of the structure. Direct entry of the expandable member through the structure wall is usually preferable to entry through a natural orifice, either because no natural orifice is available (e.g., in the case of the gallbladder) or because the entry path through the orifice is so long or tortuous that it impedes subsequent manipulation of the body structure (e.g., introduction through the esophagus into the stomach and through the vagina and cervix into the uterus). In some cases, however, it may be feasible to introduce the expandable member through a natural body orifice in such a way that permits subsequent manipulation, although it will generally be less preferred.

It will be appreciated that in certain methods of utilizing the present invention, such as during the removal of a gallbladder, a lifting device such as a compression balloon will be first inserted into the abdominal cavity to displace the liver and gallbladder for access. By providing such access to the gallbladder, it may be laparoscopically gripped the externally of the lifting balloon in the abdominal cavity and then dissected. Various mechanical extraction schemes of the abdominal cavity to allow intraperitoneal placement via small incisions or puncture sites, may be accomplished by means of either externally disposed posts or mechanical arms, or by means of inflatable bags or balloons which are expanded within the abdomen. A small opening is formed in the abdominal wall and lifting device is inserted into the abdomen through the opening in a contracted state. Once within the abdomen, the device is extended to engage an extensive area of the abdominal wall and the wall is lifted with the device. The lifting device facilitates certain operations utilizing the present invention on such organs such as the gallbladder.

The expandable member is located at the distal end of a rigid shaft which permits manipulation of the body structure from its proximal end. By "rigid" it is meant that the shaft has minimum flexibility so that manipulation at the proximal end is transmitted with minimum deflection to the distal end (where the expandable member is disposed within the body structure). Usually, the rigid shaft is composed of metal, such as surgical stainless steel, although rigid plastic shafts may also find use.

In an embodiment of the present invention, a sharp tip is provided at or near the distal end of the rigid shaft. The sharp tip may be formed as a part of or integrally with the rigid shaft, or may be formed on a separate tubular or other member which is associated with the rigid shaft. The sharp tip is provided to effect the initial penetration through the body structure wall, and the method of the present invention will usually provide for protection or shielding of the sharp tip after the penetration has been made. Specific approaches for protecting the sharp tip will be described in more detail in connection with the apparatus hereinafter.

Once inside the hollow body structure, the expandable member is expanded to fill at least a major portion of the interior volume of the hollow body structure. It will be appreciated that the degree of contact between the expandable member and the interior wall of the body structure will in large part determine the degree of control which can be exercised over the structure. Thus, by expanding the expandable member to occupy substantially the entire interior volume of the hollow body structure, a great degree of control can be obtained. In many cases, it is desirable to expand the expandable member sufficiently to distend the body structure (i.e., stretch the structure outward in all directions) so that the structure is firmly held by the expandable member on the rigid shaft. Such distension allows highly controlled manipulation and also serves to expose the dissecting plane by stretching the boundary interface between the structure and the surrounding tissue. In this way, the body structure can be pushed, pulled, turned, and otherwise manipulated during the dissection or other procedure.

The methods of the present invention further provide for removal and containment of the contents of the body structure, minimizing the risk that the contents will be accidentally spilled or leaked during the procedure. In conventional cholecystectomy and other procedures, the contents of the body structure are normally not removed since they maintain the shape of the structure and facilitate dissection. With the present invention, however, it is possible to remove the contents and thereafter expand the body structure from the interior to maintain the desired shape and facilitate dissection. Conveniently, removal of the contents of the body structure can be achieved by drainage through the shaft while containment around the site of penetration is achieved using a separate sealing member.

Referring now to FIGS. 1–4, a first embodiment of a retractor 10 will be described. The retractor 10 comprises a rigid shaft 12 having an expandable member 14 located at its distal end. As illustrated, the expandable member 14 is an inflatable balloon formed from an elastic material, such as silicone rubber, latex rubber, or the like, which when inflated can conform to the interior surface of the hollow body structure. It will be appreciated, however, that a variety of other expandable members, such as expandable coils, expandable cages, and other conformable members could be provided in place of the balloon 14. Use of the balloon is particular convenient, and it is presently contemplated as the preferred mode for carrying out the invention.

The balloon 14 can be inflated through an annular inflation lumen 16 which is defined by an inflation tube 18 mounted coaxially about the rigid shaft 12. The inflation tube 18 may itself be rigid, e.g., a metal tube, or may be a flexible polymeric sheath formed over the shaft 12. Polymeric inflation sheaths may be rigid or flexible, although flexible sheaths will usually be non-elastic so that they will not expand substantially under the inflation pressure being applied to the inflatable balloon 14. A preferred material for the inflation tube 18 is surgical stainless steel since it enhances the rigidity of the shaft 12.

The retractor 10 will further include a sharp tip 20 disposed generally at the distal end of rigid shaft 12. In this particular embodiment, the sharp tip 20 is formed at the distal end of a rigid tube 22 which can be axially translated between a distally extended configuration (as illustrated in FIG. 2) where the sharp tip 20 defines the distal tip of retractor 10 and a retracted configuration (as illustrated in FIG. 3) where the inflation balloon 14 is exposed at the distalmost point of the retractor.

The retractor 10 further comprises a coaxial sleeve 30 formed over the tube 22 and terminating in a resilient tip element 32. The resilient tip element 32 is illustrated as a metal spring 34, typically composed of stainless steel, covered by a thin plastic or elastic membrane 36. The purpose of the resilient tip is to seal about the penetration formed by the sharp tip 20 in the wall of the body structure. The resilient tip 30 can conform to the exterior of the wall about the penetration and will compress against the force of spring 34 as the tip is urged against the wall of the body structure (after penetration). Other structures, such as bellows, and accordion configurations, could also find use. The sleeve 30 itself is generally rigid with sufficient hoop strength to withstand the negative pressure of aspiration. Various polymers, such as polyethylene and polyvinyl chloride, are suitable.

Figure 2:
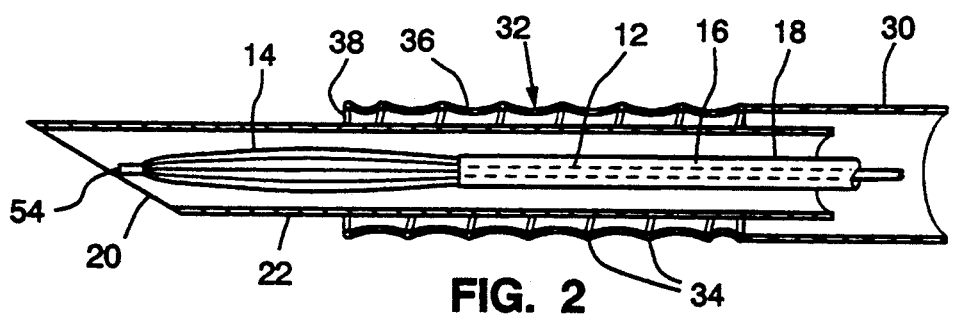
FIG. 2 is a side elevational view of the distal end of the retractor shown in FIG. 1, shown in section with a sharp tip element being advanced and the elastomeric balloon being deflated.
Figure 3:
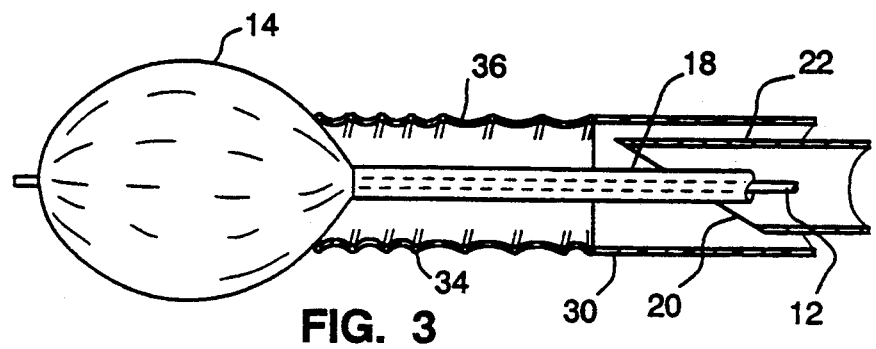
FIG. 3 is a side elevational view similar to FIG. 2, except that the sharp tip element has been retracted and the elastomeric balloon has been inflated.

The leading edge 38 of the resilient tip 32 is located over the balloon 14, usually being located approximately half way down the length of the balloon as illustrated in FIG. 2. In this way, after the balloon is fully inserted into the desired body structure, the resilient tip will necessarily be compressed. The resulting spring force assures that a relatively tight seal is achieved between the tip 33 and the outside wall of the body structure, further helping to minimize leakage.

A housing 40 is disposed at the proximal end of rigid shaft 12 and provides the necessary inflation and aspiration connections for the retractor, as well as providing means for axially translating the sharp tip 20. Axial translation is effected by a handle 42 which is attached to the proximal end of the tube 22 which carries the sharp tip 20 at its distal end. The handle 42 travels in a slot 44 formed axially in the housing 40, including detents 46 and 48 for securing the tube 22 and tip 20 in their forwardmost and rearwardmost positions. An O-ring 50 is provided at the proximal end of tube 22 to seal against the exterior of inflation tube 18. In this way, the open end of tube 22 is isolated from the outside (to inhibit gas leakage in laparoscopic procedures).

Rigid shaft 12 terminates at its proximal end in a connector 52 which may be interconnected with a suitable aspiration source (not illustrated) in order to drain the interior of the hollow body structure. The shaft 12 is typically a hollow tube having an open distal end 54 so that the contents of the body structure can be drained by aspirating through the connector 52 after the shaft 12 has been introduced, typically prior to balloon inflation.

A second connector 60 is formed on the inflation tube 18 and communicates with the annular inflation lumen 16. In this way, the balloon 14 can be inflated by applying an appropriate inflation medium, such as saline, air, or the like, through the connector 60. The inflation pressure depends on the nature of the balloon 14 as well as the nature of the body structure being expanded. In the case of gallbladders being expanded with silicone rubber balloons, the inflation pressure is typically in the range from about 0.5 to 5 pounds per square inch (psi), usually being in the range from about 1 to 2 psi. The total expanded volume of the balloon 14 (when used for gallbladder or manipulation) is typically in the range from about 25 to 75 ml, usually being from 40 to 60 ml.

A third connector port 66 is provided on the coaxial sleeve 30 and is suitable for connection to an aspiration source. In this way, the region surrounding the penetration can be aspirated through the seal formed by the resilient tip 32.

The overall dimensions of the retractor 10 are selected depending on the hollow body structure being treated. For treating the gallbladder, the retractor 10 typically has a length in the range from about 30 to 75 cm, usually being from about 40 to 50 cm. The maximum diameter of the retractor, i.e., the outside diameter of the coaxial sleeve 30, is typically less than 10 mm, preferably being in the range from about 5 mm to 7 mm.

A second embodiment 80 of a retractor is illustrated in FIG. 5. The retractor 80 comprises a rigid shaft 82 having a sharp tip 84 formed at its distal end. The rigid shaft 82 will usually be formed from metal or a rigid plastic, typically being surgical stainless steel. An inflatable balloon 86 is secured to the distal end of the rigid shaft 82 and lies just proximally of the sharp tip 84. The balloon 86 is typically composed or an elastic polymer, such as silicone rubber, and is inflatable through an inflation tube 88 which is coaxially mounted over the rigid shaft 84. The inflation tube 84 is connected through a connector port 90 located at the proximal end thereof. An outer sleeve 92 is formed coaxially about the inflation tube 88 and terminates in a resilient tip 94, typically formed from a spring 96 and elastic membrane 98. The outer tube 92 is connected to an aspiration port 100 at its proximal end to permit aspiration around the penetration formed by sharp tip 84 when inserted through the wall of the body structure.

A protection rod 104 is slidably mounted in an axial lumen 106 of the rigid shift 82. An O-ring 108 provides a sliding seal between the proximal end of rigid shift and the exterior of protection rod 104 to isolate the interior of the body structure when the retractor 80 is in use. The protection rod 104 may be extended distally from rigid shaft 82, as illustrated in broken line, in order to protect the hollow body structure from the sharp tip 84 after the retractor has been inserted through the body structure wall. The protection rod 104 can be axially advanced and retracted simply by pulling on a proximal connector 110. A stop member 112 is provided to prevent over extension of the protection rod 104. Connector 110 also provides connection to a suitable aspiration source for drainage of the interior of the body structure. The protection rod 104 includes a hollow lumen which provides a drainage path through the retractor 80.

Figure 6:
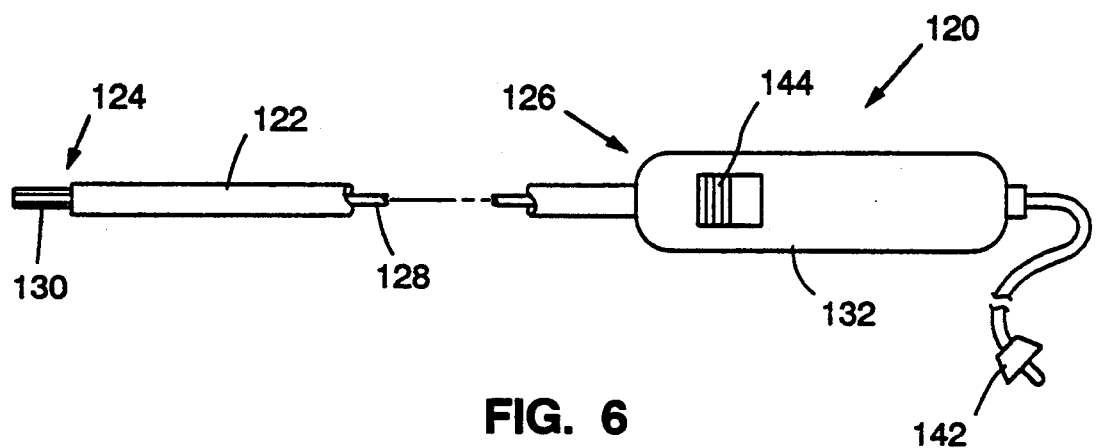
FIG. 6 is a side elevational view of a dissection device.
Figure 7:
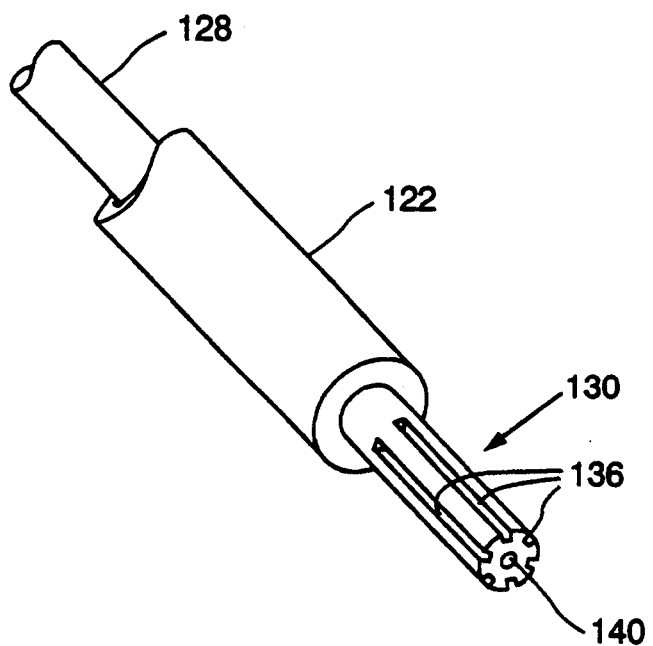
FIG. 7 is a detailed view of the distal end of the dissection device of FIG. 6, illustrating the dissection head.

Referring now to FIGS. 6 and 7, a dissection device 120 that can be used in connection with a retractor according to the present invention will be described. The dissection device 120 comprises a rigid shaft 122 having a distal end 124 and a proximal end 126. A drive shaft 128 extends through a central lumen of the shaft 122 and terminates in a dissection head 130 at its proximal end. A handle 132 is connected to the proximal end 126 of shaft 122 and includes a motor drive means capable of rotating or oscillating the drive shaft 128. The frequency of rotation (or oscillation) will typically be from about 2000 revolutions per minute (rpm) to 20,000 rpm, preferably being in the range from about 5000 rpm to 10,000 rpm. A switch 144 will be provided on handle 132 for turning on and off the dissection head 130.

The dissection head 120 is formed as a cylindrical body having a plurality of axial channels 136 formed therein. The cylindrical body has a length generally in the range from about 2 mm to 20 mm, preferably being in the range from about 5 mm to 15 mm, and a diameter in the range from about 1 mm to 10 mm, preferably in the range from about 1.5 mm to 4.0 mm. Usually, from about 4 to 10 axial channels will be formed, more usually being equally circumferentially spaced-apart.

The dissection device 120 is particularly well suited for introduction through a trocar sleeve for use in laparoscopic and other minimally invasive surgical procedures. The diameter of shaft 22 will be sufficiently small to permit such introduction, typically being 5 mm or less. The dissection device 120 is used by contacting the dissection head 30 at the dissection boundary, i.e., the interface between the tissue and body structure to be dissected from the tissue, and initiating rotation and/or oscillation of the head. Use of the high frequency rotation or oscillation has been found to provide a relatively clean separation between the tissue and body structure with minimal risk of bleeding, perforation, or other undesirable injuries.

Preferably, the dissection device 20 will further include an electrode 140 at its distal tip. Electrode 140 can be connected to a conventional electrocautery power supply, typically a monopolar power supply through a connector 142 which is disposed at the proximal end of the handle 132. Thus, the dissection device 20 can be used to cauterize any cuts or tears which are accidentally caused, without need to introduce a separate electrocautery device.

Figure 8C:
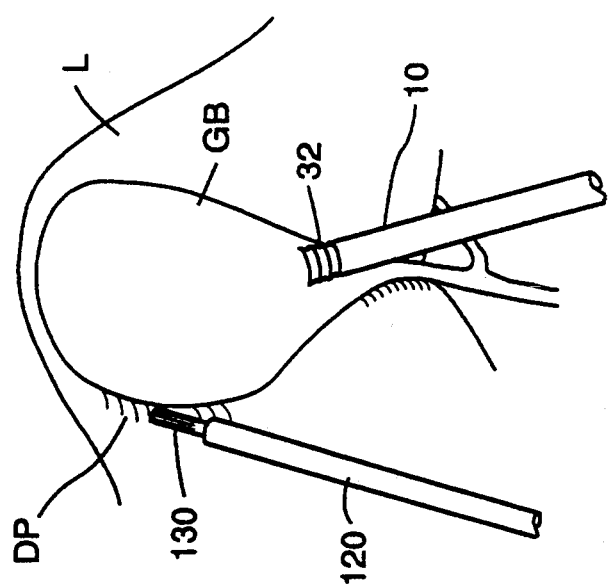
FIGS. 8A through 8C illustrate the method of the present invention for manipulating and dissecting a gallbladder.
Figure 8B:
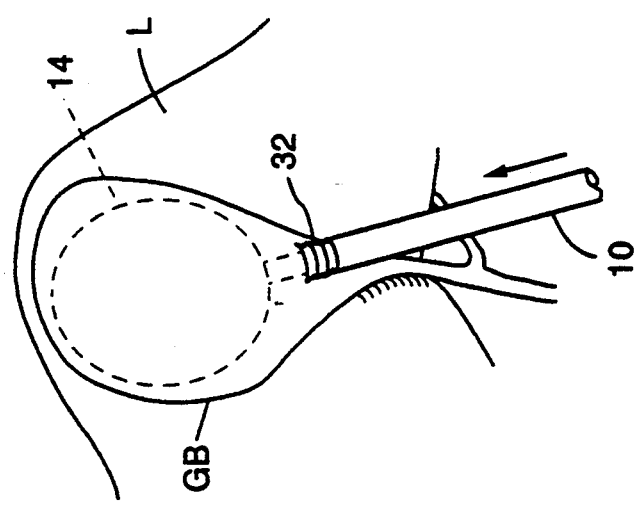
Figure 8A:
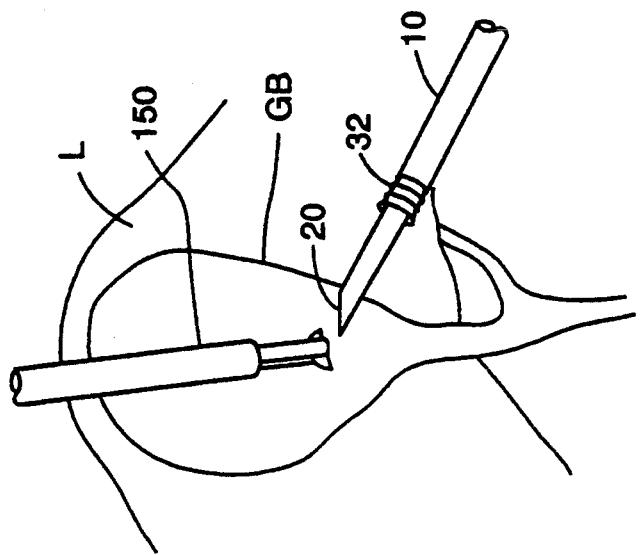

Referring now to FIGS. 8A through 8C, use of the retractor 10 and the dissection device 120 for performing a gallbladder removal procedure (cholecystectomy) will be described. The figures illustrate the gallbladder GB being dissected from the liver L. The instruments utilized, including both the retractor 10 and the dissection device 120, will have been introduced through conventional trocar sheaths in a well known manner for performing laparoscopic cholecystectomy.

Initially, a portion of the outside wall of the gallbladder GB is grasped with a conventional forceps grasper 150, as illustrated in FIG. 8A. The sharp tip 20 of the retractor 10 is then penetrated through the wall of the gallbladder GB next to the region which is held in place by the graspers 150.

After the penetration has been achieved, the retractor 10 is advanced forward until the resilient tip 32 forms a seal about the site of penetration, as illustrated in FIG. 8B. The sharp tip 20 is retracted by axially translating the tube 22 in a proximal direction, and the contents of the gallbladder (bile) is withdrawn through the interior lumen of the shaft 12. After the contents have been largely drained, the balloon 14 is inflated (as illustrated in broken line in FIG. 8B) to fill the void which has been left and expand the gallbladder GB, usually distending the gallbladder slightly to improve control and access. The retractor 10 may then be used to manipulate the gallbladder GB and expose the dissection plane DP, i.e. the interstitial plane between the gallbladder and the liver bed L.

The tissue dissection device 120 is next introduced, and the dissection head 130 contacted with the dissection plane DP (FIG. 8C). The dissection head 130 is actuated and used to carefully separate the exposed wall of the gallbladder GB from the liver bed L. It will be appreciated that the retractor 10 will be constantly repositioned to expose the dissection plane DP in an optimum manner. The dissection is continued until the gallbladder GB is completely detached from the liver bed L and other surrounding tissue. The inflated balloon 14 can then be deflated, the retractor 10 withdrawn, and the gallbladder removed through a trocar sleeve in a conventional manner.

FIGS. 9, 10 and 11 are perspective views of a retractor shown in place within the abdominal cavity with a body, with parts broken away for illustration and laparoscopic forceps extended into gripping engagement with the gallbladder. These figures sequentially illustrate the steps of introducing the retractor laparoscopically into the abdominal cavity and, into a gripping engagement with the gallbladder. Referring to FIG. 9, forceps 200 are laparoscopically extended into gripping engagement with the gallbladder 201. The procedure is viewed through an endoscope 203 located within an abdominal balloon lifting device 203a.

With the gallbladder so gripped, a retractor 202 is extended into the abdominal cavity in piercing engagement with the gallbladder, as depicted by the arrow line in FIG. 10. The retractor 202 shown takes the form of a dual lumen hollow shaft having a sharpened open end through which the contents of the gallbladder may be drawn and an annular balloon which may be inflated through the lumen of the hollow shaft communicating therewith.

Once the retractor has been used to evacuate the contents of the gallbladder, the balloon 204 is inflated and assumes internal gripping engagement with the gallbladder. The retractor may then be manipulated, thus maneuvering the gallbladder within the abdominal cavity or exerting tension on it as depicted by the arrow line in FIG. 11. Depending upon the size of the gallbladder, removing the organ may require some enlargement of the incision through which the retractor extends. The forceps are released from the gallbladder to permit its manipulation using only the retractor. The entire procedure is viewed through the endoscope 203. Following deflation and removal of the balloon, the gallbladder is seized by forceps for further manipulation.

Figure 12:
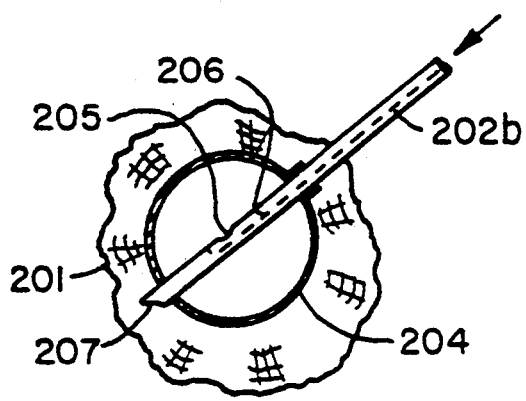
FIG. 12 shows a retractor having an elastomeric balloon attached to the distal end of a hollow shaft.
Figure 13:
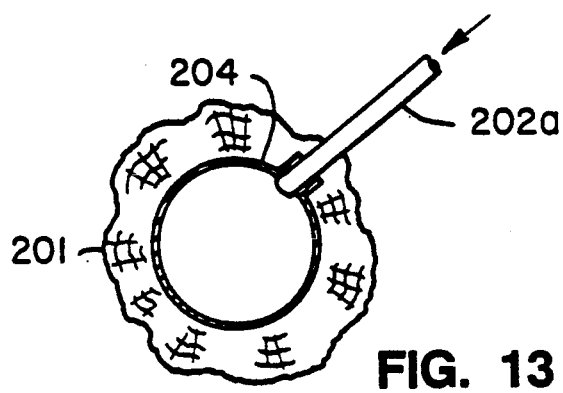
FIG. 13 shows a retractor having an elastomeric balloon attached to a hollow shaft at both ends of a diameter of the balloon, and shows how the hollow shaft is present in the gall bladder during manipulation of the gall bladder.

FIGS. 12 and 13 show two alternative forms of the retractor 202. The retractor of FIG. 13 corresponds to that of FIG. 12 except that the hollow shaft 202a has a single lumen only for inflation of the balloon 204 and that the hollow shaft 202a does not extend through the balloon. Thus, the embodiment in FIG. 13 cannot be used to evacuate the gallbladder, and the balloon is less well supported, but no rigid parts are left in the gallbladder during manipulation of the gall bladder. In FIG. 12, the hollow shaft 202b accommodates a separate channel 206, communicating with the interior of balloon 204 through orifice 205. The end of the hollow shaft 202b accommodates orifice 207 through which the contents of gallbladder 201 may be evacuated. During manipulation of the gall bladder, a considerable length of the hollow shaft remains in the gall bladder.

Figure 14:
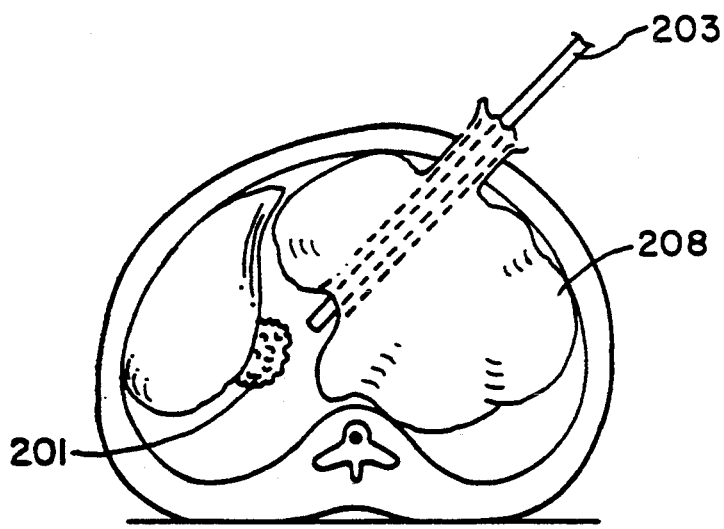
FIG. 14 illustrates a modification of the method illustrated in FIGS. 9 through 11 wherein the gallbladder is viewed from the exterior of the abdominal lifting device.

FIG. 14 is a cross-sectional view similar to the above, showing a modified version of the invention wherein the endoscope 203 extends fully through a balloon 208 which serves as an abdominal lifting device. The gallbladder 201 is then viewed directly, rather than through the balloon 208.

Figure 15:
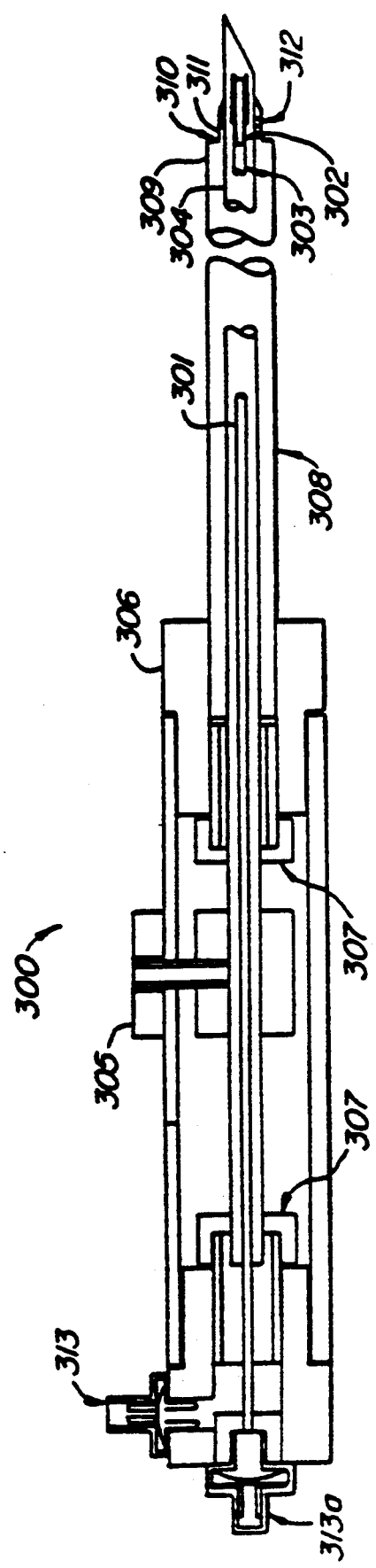

Referring to FIG. 15, there is shown a retractor for insertion into the gallbladder for draining the contents thereof and inflating a balloon for manipulation. This embodiment permits removal of all rigid or semi-rigid structures from within the gallbladder (or other organ) prior to manipulation to avoid the risk of organ injury. The further improvement is provided in that the needle tip used for organ entry is retracted out of the organ to prevent injury.

Referring to FIG. 15, the retractor 300 is a rigid structure which allows for control of the displacement of the attached organ. Therefore, the retractor may be constructed of metal or of other suitable rigid material, whereby the rigidity is imparted by one or more of the three concentric tubular members which comprise the retractor.

The innermost tube 301 holds an elastomeric member 302, which will be inflated inside the organ to hold and distend the organ for manipulation. An elastomeric balloon is preferred because of its initial small profile upon entry into the organ and its expansion capacity upon inflation to fill the inside of the organ. The elastomeric member 302 is shown in an inverted position within the innermost tube 301. The elastomeric member 302 is everted into the organ after protrusion of a small length of the distal end 303 of the innermost tube 301 into the organ. This is an improvement in that it minimizes the length of the innermost tube which must be placed into the organ prior to inflation. The end of the elastomeric member 302 is bonded to the distal end 303 of the innermost tube 301 in a suitable manner, for example by use of adhesive, adhesive with an outer plastic shrink wrapping, adhesive with an outer suture winding, and the like. The innermost tube 301 may be made of a rigid plastic material such as nylon, PVC, polyethylene, and the like, or, most preferably, stainless steel.

The innermost tube 301 is concentrically disposed within a tubular needle 304 having a sharp point for piercing the organ. The needle 304 may extend to completely enclose the innermost tube 301, in the closed configuration of the retractor 300, and then may be mechanically retracted proximal to the distal end 303 of the innermost tube 301 to expose the innermost tube to the interior of the organ. Preferably, the needle 304 is made of stainless steel. Retraction of needle 304 is accomplished by exterior handle 305 affixed to needle 304 within the housing 306 at the proximal end of the retractor 300. Seals 307 are provided to allow for movement of the tubular needle 304 in a gas tight manner.

The outermost tube 308 is concentric with tubular needle 304 and is fixed in position with respect to the innermost tube 301, with the distal end 309 of the outermost tube 308 being approximately flush with the distal end 303 of the innermost tube 301. The outermost tube 308 is stepped down to form a step 310 at its distal end, with the inner diameter at the step providing a slip fit with the outer diameter of the tubular needle 304. The length of the step is preferably about 0.1 to 0.15 inches (2.5 to 4 mm).

The advantage of the step 310 is to provide a mechanical stop during insertion of the retractor 300 into the organ. When the needle tip of the tubular needle 304 is extended and used to puncture an organ, the needle tip and the stepped down portion 311 of the outer tube 308 easily enter the organ wall. When the outer wall of the organ impacts the step 310 on the outer tube 308, the forward progress of the retractor 300 is halted, thereby guarding against excessive needle travel and puncture of the back wall of the organ.

The stepped down portion 311 may contain radial holes 312 or slots placed around its circumference to assist in drainage of the organ contents when the needle tip is retracted. Vacuum suction may be applied in the volume between the outermost tube 308 and the needle 304, as well as in the volume between the needle 304 and innermost tube 301, by application of a vacuum at aspiration port 313 which is in communication with the volume between the innermost tube 301 and tubular needle 304. Upon retraction of the needle 304 into the outermost tube 308, aspiration will also be effective within the volume at the distal ends between the needle 304 and the outermost tube 308.

The outermost tube 308 is also preferably made of a rigid material such as plastic, (nylon, PVC, polyethylene and the like) or stainless steel.

The housing 306 at the proximal end of the retractor 300 accommodates the port 313a and the fittings for inflation of the elastomeric member 302 through the interior of the innermost tube 301. The tubular needle 304 may be locked in its forward (extended) position for entry into the organ by a suitable locking mechanism (not shown) and unlocked and retracted prior to the balloon inflation.

The tubular members 301, 304 and 308 are sealed on their interior volumes such that no gas leaks occur when the retractor is introduced into the abdomen or organ for laparoscopic surgery.

Inflation of the elastomeric member 302 may be accomplished using a separate inflation device such as a syringe or a pump. A pump may be built directly into the housing 306.

Figure 16:
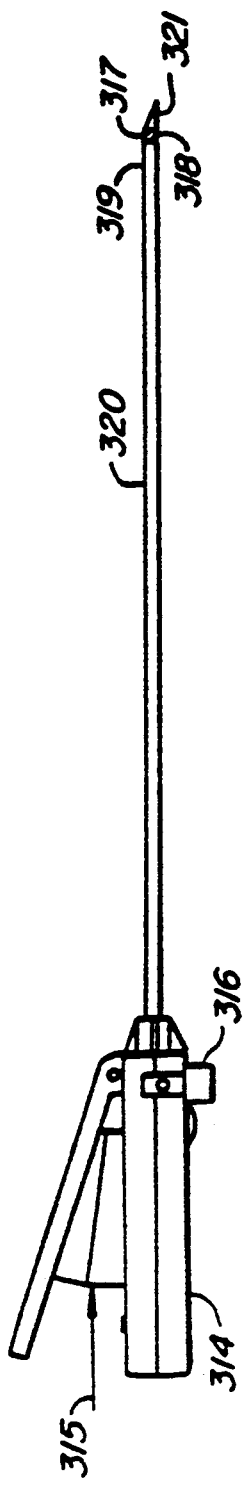

Referring to FIG. 16 there is shown an alternative embodiment of the retractor of FIG. 15 wherein a pump is built into the housing 314. Pumping is actuated by a bellows 315 and withdrawal of contents of the interior of the organ is conducted through aspiration port 316. There are shown the step 317 and radial holes 318 at the distal end 319 of the outermost tube 320. Only the tip of the tubular needle 321 is shown.

Figure 17A:
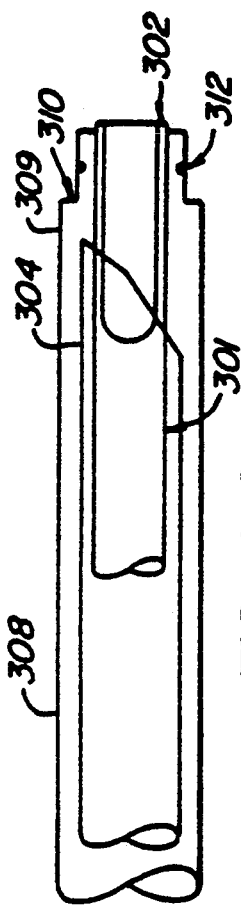
FIGS. 17A, 17B, and 17C illustrate the use of the retractors shown in FIGS. 15 and 16.
Figure 17B:
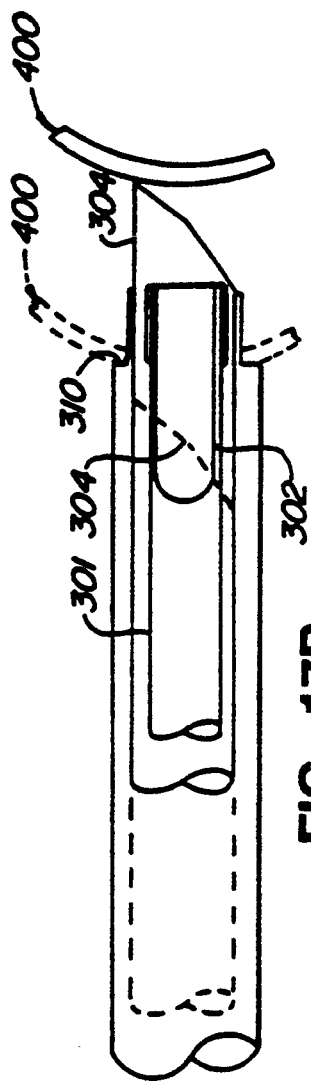
Figure 17C:
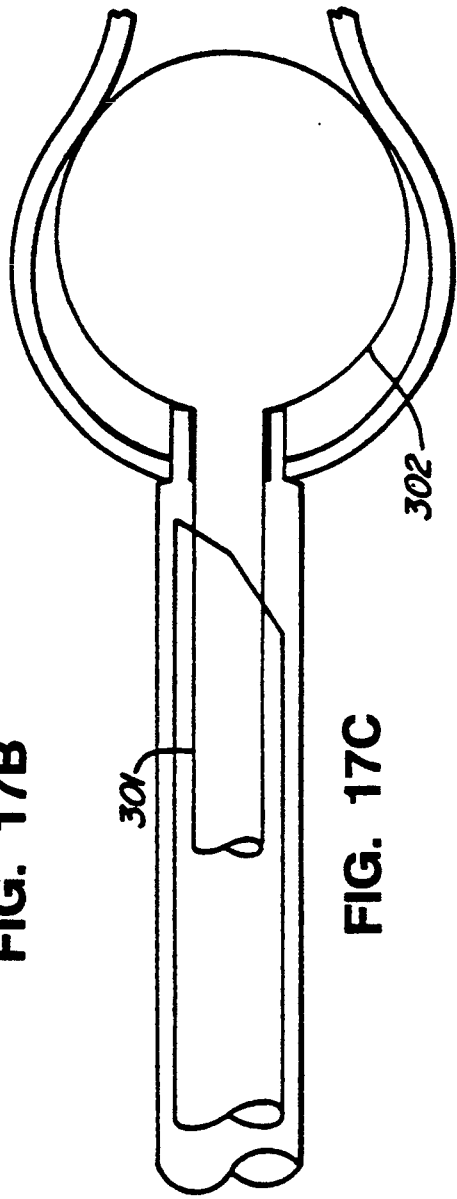

Referring to FIGS. 17A, 17B, and 17C there is shown the retractor of FIGS. 15 or 16 in use. For convenience, the same numerals on corresponding elements as described in FIG. 15 will be used in connection with the description of FIG. 17. Referring to FIG. 17A, the distal end 309 of the outermost tube 308 is advanced into an abdominal cavity (not shown) through a properly sized trocar with the needle 304 retracted into the tube 308 to protect the needle tip. The trocar seals against the tube 308 to maintain pneumoperitoneum.

The needle 304 is advanced out of the outer tube 308 (FIG. 17B) and a grasping instrument (not shown) stabilizes the wall of the organ 400 as the extended needle punctures through the wall and stops at the end of the outer tube step 310. The needle is then unlocked from its extended position and retracted (dotted outline in FIG. 17B) then suction is applied through the aspirator port (not shown) which drains the fluid contents from the organ.

Air is then pumped through the innermost tube 301 (FIG. 17C) to evert the balloon 302 out of the innermost tube into the organ and pumping is continued to inflate the balloon within the organ. The organ may now be manipulated for dissection and isolation for removal. Following organ dissection, the balloon is deflated to allow the organ to be detached.

Referring to FIGS. 18 and 18A, another embodiment of the retractor is shown having two concentric tubes instead of three, whereby electrocautery is used to enter the organ instead of a needle. The inner tube 450 holds an inverted elastomeric balloon 451 and tube 450 is connected to a slide arrangement within the handle 452 which allows for extension and retraction with respect to the outer tube 453. The mechanism in the handle 452 provides a locking mechanism 454A and B to lock the inner tube 450 in an extended position. The proximal end of the inner tube 450 accommodates inflation port 455 for inflating the balloon 451. A drainage port 456 is provided for evacuating the contents of the organ by aspiration.

The inner tube 450 is preferably made of a rigid material such as stainless steel with an outer insulating sleeve which is electrically insulated with an insulator such as polyvinyl chloride, polyethylene, or nylon. The outer tube 453 is also preferably stainless steel but may be made of another electrically conducting material and provides a loose fit with the inner tube 450. The outer tube 453 is electrically insulated on the outside with insulation 453A, leaving a small portion of the distal end (preferably 2 to 3 millimeters of length) uninsulated at the tip.

Referring to the detail of the tip in FIG. 18A, the exposed distal tip 457 is cut away, preferably so that only an arc of less than about 180 degrees of the circumference of the outer tube 453 remains. This enables a small curved slit to be cut in the organ wall by cauterization, instead of a full circle. This aids sealing the organ wall against the shaft of the retractor and minimizes the amount of heat-necrosed tissue that may cause the entry hole to enlarge upon traction and manipulation of the retractor.

An electrocautery connector 458 is provided in the handle 452 to allow hookup to an electrocautery generator (not shown).

In use, the inner tube 450 is initially withdrawn (preferably approximately 1-2 cm) into the outer tube 453 during entrance through the wall of the organ by cauterization. This prevents the inner tube 450 and balloon 451 from being heated by the tip of the outer tube during cautery use. Following entrance of the outer tube into the organ, suction aspiration of the organ contents is performed through port 456. The inner tube 450 is then advanced forward and locked in an extended position. Air is pumped through port 455 to evert and inflate the balloon 451 in preparation for the organ manipulation.

Referring to FIG. 19, another embodiment of the organ balloon manipulator is shown. A needle 500 is provided within a rigid inner tube 501 and a concentric rigid outer tube 502. An elastomeric sleeve 503 is attached having one edge attached to the distal ends of the inner and outer tubes, respectively. A seal 504 is provided at the proximal end of the retractor to allow the inner tube 501 to translate longitudinally with respect to the outer tube 502 while maintaining a gas-tight seal. A locking mechanism 505A and 505B allows the needle 500 to be positioned and locked with respect to inner tube 501, so that the needle 500 is in an armed configuration. An inflation port is provided for 506 to provide for inflation of the elastomeric sleeve 503 and an aspiration port 507 is provided for evacuation of the organ contents.

In use, the needle 500 is locked in a forward position and the retractor is advanced to puncture through the organ wall 510 (FIGS. 19A and 19B). The needle 500 is unlocked and withdrawn at least partially into the inner tube 501 to prevent injury to the organ. The retractor is further advanced until the outer tube 502, lies within the cavity of the organ.

The elastomeric sleeve balloon 503 is inflated (FIG. 19B) and inner tube 501 is retracted with respect to the outer tube 502 until the tips of the inner and outer tubes meet. This action causes the balloon 503 to take on a toroidal shape and removes all rigid tubes from inside the organ.

Figure 20A:
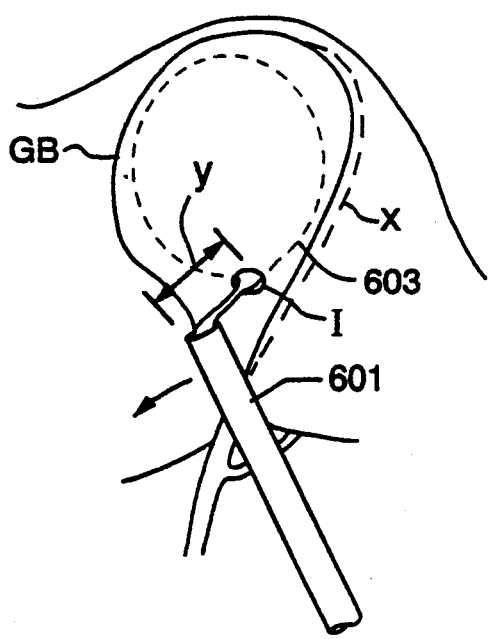
FIGS. 20A and 20B show the excessive distensibility of the elastomeric balloon and the consequences thereof in a retractor having an elastomeric balloon attached to the distal end of a hollow shaft.

The embodiments shown in FIGS. 13, and 15 through 19 are improved relative to the embodiments shown in FIGS. 1 through 5, and 12 in that rigid structures are removed from the organ before retractor is used to manipulate the organ. Removing rigid structures from the organ before manipulation begins reduces the risk of a rigid structure penetrating or otherwise injuring the organ, but has the disadvantage that all the manipulation force is transferred to the balloon, and hence to the organ, through a single point of attachment between the balloon and the rigid parts of the retractor. The resulting concentration of the manipulating force causes the balloon used in the embodiments shown in FIGS. 13, and 15 through 19 to be excessively distensible near where it is attached to the rigid part of the retractor. This is illustrated in FIG. 20A, which shows a balloon 603 attached near the distal end 605 of a rigid, hollow shaft 601. The hollow shaft 601 corresponds to the hollow shaft 202a in FIG. 13, the innermost tube 301 in FIG. 15, the inner tube 450 in FIG. 18, and the rigid outer tube 502 in FIG. 19. The balloon 603 corresponds to the balloon 204 in FIG. 13, the elastomeric member 302 in FIG. 15, elastomeric balloon 451 in FIG. 18, and the elastomeric sleeve 503 in FIG. 19.

The excessive distensibility of the balloon seriously impairs the surgeon's control over the organ. To displace the organ a nominal amount x, the surgeon is forced to displace the distal end of the hollow shaft a considerably greater distance y. To displace the organ by a desired amount may require that the balloon be stretched to its limit, with the consequent risk of the balloon rupturing.

Figure 20B:
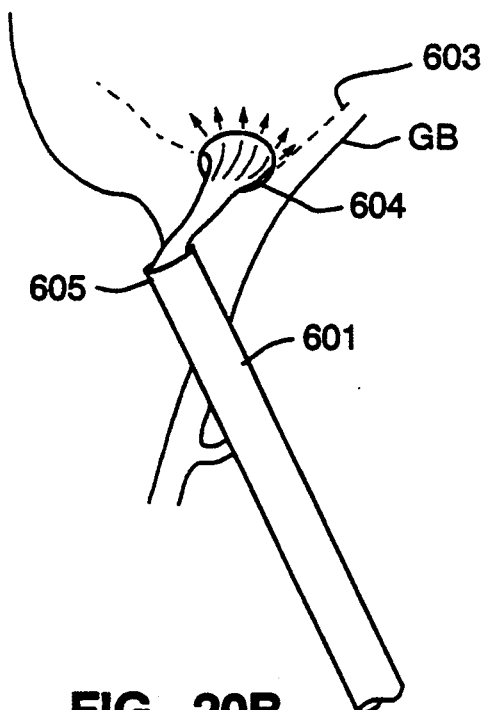

As a further consequence of the excessive distensibility of the balloon 603 near the attachment point to the hollow shaft 601, the manipulating force causes the balloon to cone outwards from the attachment point 605 on the hollow shaft, through the entry hole I in the organ GB (the gall bladder is shown as an example in FIG. 20B) up to its fully-inflated diameter inside the organ. When the retractor is manipulated to manipulate the organ, the conical portion 604 of the balloon acts as a wedge against the entry hole, widening the entry hole, and allowing the inflated balloon to escape from the organ. Widening the entry hole may cause the organ wall at the entry hole to tear, and may render the organ incapable of retaining the balloon when the balloon is re-inserted into the organ.

As a final consequence of the excessive distensibility of the balloon 603 near the attachment point to the hollow shaft 601, an attempt to turn the organ by applying a manipulating torque about the longitudinal axis of the hollow shaft causes the balloon to twist near the attachment point to the hollow shaft. This results in a significantly reduced torque being applied to the organ itself, and can result in rupture of the balloon and/or injury to the entry hole.

Figure 21A:
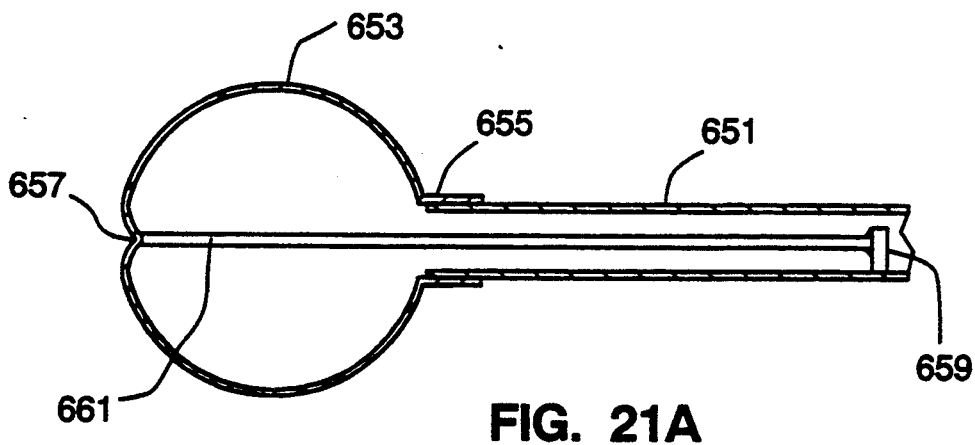
FIGS. 21A and 21B show a first embodiment of a retractor according to the invention with the elastomeric balloon in its expanded state and its inverted, collapsed state, respectively.
Figure 21B:
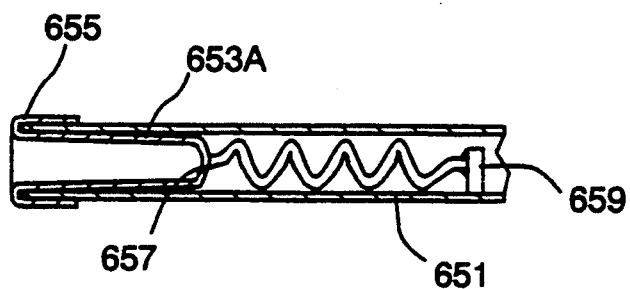

A first embodiment of an improved retractor according to the invention is shown in FIGS. 21A and 21B. In FIG. 21A, which shows the retractor with the balloon in its expanded state, a hollow shaft 651 is shown. The hollow shaft 651 corresponds to the hollow shaft 202a in FIG. 13, the innermost tube 301 in FIG. 15, the inner tube 450 in FIG. 18, and the rigid outer tube 502 in FIG. 19. Attached to the distal end 655 of the hollow shaft 651 is the balloon 653. The balloon 653 corresponds to the balloon 204 in FIG. 13, the elastomeric member 302 in FIG. 15, elastomeric balloon 451 in FIG. 18, and the elastomeric sleeve 503 in FIG. 19. With this correspondence of elements, the embodiments shown in FIGS. 13, and 15 through 19 can be modified to incorporate the improvements now to be described.

The tether anchor 659, which is preferably a small metal or plastic bracket, is attached to the bore of the hollow shaft 651. The tether 661, which is piece of a flexible, inelastic material, such as a nylon thread, interconnects the distal tip 657 of the balloon to the tether anchor. Alternatively, the tether anchor can be omitted, and the tether can be attached directly to the bore of the hollow shaft by, for example, a suitable adhesive.

FIG. 21B shows the retractor with the balloon in its collapsed state inverted within the bore of the hollow shaft 651. The balloon in its collapsed state is indicated by the numeral 653A. The tether anchor 659 is located proximally with respect to the proximal extent of the inverted balloon 653A, and the tether in its slack state, indicated by the numeral 661A, is accommodated in the bore of the hollow tube between the proximal extent of the inverted balloon and the tether anchor.

The length of the tether 661 is chosen so that it is about equal to the sum of the distance between the tether anchor 659 and the distal end 655 of the hollow shaft, and the length of the balloon 653 in its inflated state. When the balloon is inflated to its expanded state, slack is removed from the tether until the tether is fully extended and is under tension.

When the balloon 653 of the retractor according to the invention is deployed inside an organ, and the hollow shaft 651 is manipulated to manipulate the organ, the tether 661 limits the maximum distance of the distal tip 657 of the balloon from the distal end 655 of the hollow shaft to a distance corresponding to the length of the balloon in its unstressed expanded state.

A manipulation force applied proximally in the direction of the axis of the hollow shaft 651 causes some distention of the balloon 653, but the amount of distention is substantially reduced by applying the manipulation force to the balloon at two points, i.e., at the connection between the balloon and the tether 661, and at the connection between the balloon and the distal end 655 of the hollow shaft. Any distal excursion of the distal tip 657 of the elastomeric balloon in response to a manipulation force in the proximal direction is limited by the tether. Limiting distal excursion of the distal tip of the balloon further reduces distention. On the other hand, the tether, being flexible, allows the distal tip of the elastomeric balloon to move freely in the proximal direction in response to a manipulation force in the distal direction. There is thus minimal risk of the tether puncturing or otherwise injuring the organ when a manipulation force is applied in the distal direction.

As well as preventing distention of the balloon 653, the flexible tether 661 provides some additional stiffness to the balloon in directions perpendicular to the axis of the hollow shaft 651. A manipulation force in a direction perpendicular to the axis of the hollow shaft displaces the distal tip of the balloon and the distal part of the tether away from the axis of the hollow shaft. This offset enables the tether to exert force perpendicular to the shaft axis to resist the perpendicular manipulation force.

Applying the manipulation force to the elastomeric balloon 653 at two points (the connection between the balloon and the tether 661 and the connection between the balloon and the distal end 655 of the hollow shaft) reduces the peak stress in the balloon. This significantly reduces distention of the balloon, which provides the surgeon with greater control and reduces the likelihood of the balloon rupturing. Moreover, the tether enables the balloon to maintain a substantially spherical or spheroidal shape, rather than assuming a conical shape, when subject to manipulation forces. With a spherical or spheroidal shape, the balloon cannot act as a wedge and enlarge the entry hole. The balloon thus stays firmly anchored within the organ.

The flexible tether in the first embodiment of the retractor according to the invention substantially reduces distention of the balloon by the manipulation force. However, unlike the embodiments shown in FIGS. 1 through 5, and 12, the first embodiment of the retractor according to the invention there is no part of the hollow shaft inside the organ while manipulation is carried out. Thus, compared with the embodiments shown in FIGS. 1 through 5, and 12, the risk of puncturing or otherwise injuring the organ is therefore considerably reduced.

Figure 22A:
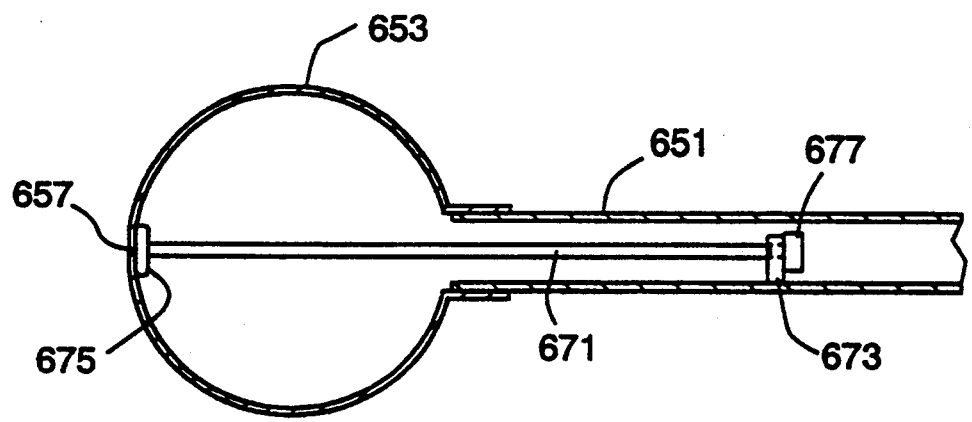
FIGS. 22A and 22B show an alternative embodiment of a retractor according to the invention with the elastomeric balloon in its expanded state and its inverted, collapsed state, respectively.
Figure 22B:
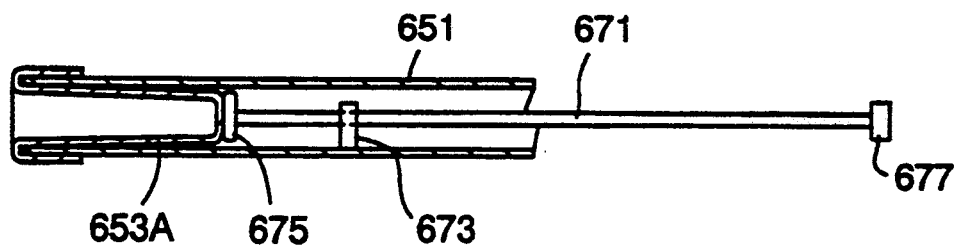

FIGS. 22A and 22B show an alternative embodiment of a retractor according to the invention. In this embodiment, the tether 671 is a rigid shaft of metal or plastic. The tether is free to slide axially in the tether anchor 673. The tether anchor is preferably a small metal or plastic bracket fixed to the bore of the hollow shaft 651 and includes a hole through which the tether is free to slide.

The distal end 675 of the tether 671 is flattened, or the tether is otherwise provided with a broad, blunt nose, to facilitate attaching the distal end 675 to the distal tip 657 of the balloon 653, preferably by means of a suitable adhesive. The flattened distal end of the tether also provides the retractor with a broad, blunt nose to reduce the possibility of injuring the organ. The distal end 675 is preferably flattened to the maximum extent that will easily pass through the bore of the hollow shaft 651. The proximal end of the tether 671 includes a stop 677 to limit the extent to which the tether can slide distally through the tether anchor.

FIG. 22B shows the alternative embodiment of the retractor with the balloon in its collapsed state, inverted in the bore of the hollow shaft 671. The balloon in its collapsed state is indicated by the numeral 653A. The tether anchor 673 is located in the bore of the hollow shaft proximally with respect to the proximal extent of the inverted, collapsed balloon 653A. When the balloon is in its collapsed state, the tether is accommodated in the bore of the hollow shaft proximally of the tether anchor.

The length of the tether 671 is chosen so that it is about equal to the sum of the distance between the tether anchor 673 and the distal end 655 of the hollow shaft, and the length of the balloon 653 in its inflated state. Everting and inflating the balloon slides the tether distally through the tether anchor. When the balloon is in its inflated state, the stop 677 engages with the tether anchor, and the tether defines the length of the inflated balloon.

When the balloon 653 of the retractor according to the alternative embodiment of the invention is deployed inside an organ, and the hollow shaft 651 is manipulated, the tether 671 limits the maximum distance of the distal tip 657 of the balloon from the distal end 655 of the hollow shaft to a distance corresponding to the length of the balloon in its unstressed expanded state.

A manipulation force applied proximally in the direction of the axis of the hollow shaft 651 causes some distention of the balloon 653, but the amount of distention is substantially reduced by applying the manipulation force to the balloon at two points, i.e., at the connection between the balloon and the tether 671 and at the connection between the balloon and the distal end 665 of the hollow shaft. Any distal excursion of the distal tip 665 of the elastomeric balloon in response to a manipulation force in the proximal direction is limited by the tether. Limiting distal excursion of the distal tip of the elastomeric balloon further reduces distention. On the other hand, the tether, being free to slide proximally through the tether anchor 673, allows the distal tip of the elastomeric balloon to move freely in the proximal direction in response to a manipulation force in the distal direction. There is thus minimal risk of the tether puncturing or otherwise injuring the organ when a manipulation force is applied in the distal direction.

The distal tip 657 of the balloon has some freedom of movement in directions perpendicular to the axis of the hollow shaft 651. However, the freedom of movement in these directions is restricted by the tether 671 contacting the distal end 655 of the hollow shaft. When the tether contacts the distal end of the hollow shaft, the tether cannot move further, whereupon the tether increases the stiffness of the balloon in the direction perpendicular to the axis of the hollow shaft.

Applying the manipulation force to the elastomeric balloon 653 at two points (the connection between the balloon and the tether 671 and the connection between the balloon and the distal end 655 of the hollow shaft) reduces the peak stress in the balloon. This significantly reduces distention of the balloon, which provides the surgeon with greater control, and reduces the likelihood of the balloon rupturing. Moreover, the tether enables the balloon to maintain a substantially spherical or spheroidal shape, rather than assuming a conical shape, when subject to a manipulation force. With a spherical or spheroidal shape, the balloon cannot act as a wedge and enlarge the entry hole. The balloon thus stays firmly anchored within the organ.

Unlike the embodiment shown in FIGS. 21A and 21B, the alternative embodiment leaves a rigid shaft (i.e., the rigid tether 671) inside the organ while the organ is manipulated. Unlike the embodiments shown in FIGS. 1 through 5, and 12, the rigid tether inside the organ is free to slide proximally relative to the hollow shaft 651, and has some freedom of movement in directions perpendicular to the axis of the hollow shaft. Finally, the rigid shaft is provided with a wide, blunt nose. Thus, the risk of the alternative embodiment of the retractor puncturing or otherwise injuring the organ is considerably reduced compared with the embodiments shown in FIGS. 1 through 5, and 12.

The preferred embodiment of a retractor according to the invention is shown in FIGS. 23A and 23B. The retractor is shown with the balloon 703 in its expanded state in FIG. 23A. The distal part of the hollow shaft 701 is shown. The hollow shaft 701 corresponds to the hollow shaft 202a in FIG. 13, the innermost tube 301 in FIG. 15, the inner tube 450 in FIG. 18, and the rigid outer tube 502 in FIG. 19. Attached to the distal end 705 of the hollow shaft 701 is the elastomeric balloon 703. The elastomeric balloon 703 corresponds to the balloon 204 in FIG. 13, the elastomeric member 302 in FIG. 15, elastomeric balloon 451 in FIG. 18, and the elastomeric sleeve 503 in FIG. 19. With this correspondence of elements, the retractors shown in FIGS. 13, and 15 through 19 can be modified to incorporate the preferred embodiment of the invention that now will be described.

The tether anchor 704 is formed in the hollow shaft 701 by reducing the cross-sectional area of the hollow shaft at a point proximal with respect to the proximal extent of the inverted collapsed balloon 703A (FIG. 23B). The tether anchor is preferably formed by crimping the hollow shaft, although alternative ways of reducing the cross sectional area of the hollow shaft, such as fixing a collar in the bore of the hollow shaft, can be used. The cross section of the tether anchor 704 preferably includes two or more diametrically-opposed flats 706, as shown in FIG. 23C. The purpose of the flats will be described below.

The tether 711 is a rigid tube, preferably of metal, such as stainless steel, that is free to slide axially within the bore of the hollow shaft 701. The tether is preferably of a generally circular cross section and has a diameter greater than the distance between the opposing flats 706 in the hollow shaft, as shown in FIG. 23D.

The cross-sectional area of the tether 711 is reduced over a flattened portion 712 of the length of the tether to provide two or more diametrically-opposed flats 714, corresponding to the two or more diametrically-opposed flats 706. In the preferred embodiment, the flats 714 are formed by compressing the tether across a diameter. The resulting cross section of the portion 712 can be seen in FIG. 23C. Juxtaposing the flats 714 on the tether and the flats 706 on the hollow shaft enables the tether to slide axially relative to the hollow shaft, but prevents the tether from rotating relative to the hollow shaft. This enables a torque applied to the hollow shaft to be transmitted to the tether.

The tether slides over an axial distance defined by the length of the flattened portion 712. Distal sliding is limited by the shoulder 716, and proximal sliding is limited by the shoulder 718.

The distal tip 707 of the balloon is attached to the distal end 708 of the tether. A suitable adhesive can be used. Alternatively, and preferably, the attachment shown in FIG. 23A can be used. In this, the distal tip 707 of the balloon is placed in contact with the distal end of the tether. A substantially spherical rigid object, for example, the ball bearing 720, is placed in contact with the distal tip of the balloon, and is inserted together with the distal tip of the balloon a few millimeters into the distal end of the bore 710 of the tether. The tether is then crimped at a point distal relative to the position of the ball bearing. The resulting crimp 722 retains the ball bearing 720 and the distal tip 707 of the balloon in the bore of the tether.

The retractor is shown with the balloon 703 in its inverted, collapsed state in FIG. 23B. The balloon in its inverted, collapsed state is indicated by the numeral 703A. The tether is slid to its most-proximal extent, further proximal sliding being inhibited by contact between the shoulder 718 and the tether anchor 704.

The retractor is shown with the balloon in its everted, expanded state in FIG. 23A. Inflating the balloon 703 has slid the tether 711 distally in the bore of the hollow shaft 701. Further distal sliding is inhibited by contact between the shoulder 716 and the tether anchor 704.

The length of the flattened portion 712 of the tether is set so that when the balloon 703 is fully inflated, the distal excursion of the distal tip 707 of the balloon is limited to less than the normal inflated length of the balloon. Limiting the distal excursion of the distal tip of the balloon causes the balloon to assume the apple-shaped cross section shown in FIG. 23A.

Giving the balloon an apple-shaped cross section has two advantages. When a manipulating force is applied in the proximal direction, the line of contact between the apple-shaped balloon and the organ is radially separated from the entry hole. Applying the manipulating force to the organ at a point radially separated from the entry hole reduces stress on the entry hole, and further reduces the possibility of the balloon tearing the entry hole. Moreover, a very large manipulation force is required to deform the apple-shaped balloon into the conical shape that can expand and possibly tear the entry hole.

When a manipulating force is applied in the distal direction, the distal part of the apple-shaped balloon separates the organ from the distal end 708 of the tether. The preferred embodiment of the retractor according to the invention places a rigid shaft (i.e., the tether 711) inside the organ during manipulation procedures. However, the rigid tether is free to slide proximally until it is fully surrounded by the hollow shaft 701, the rigid tether has some freedom of movement in directions perpendicular to the axis of the hollow shaft, the rigid tether has a wide, blunt nose, and, finally, is protected by the apple-shaped balloon. Thus, the risk of the tether injuring the organ is significantly reduced compared with the embodiments shown in FIGS. 1 through 5, and 13.

The lengths of the tethers 661 and 671 in the embodiments shown in FIGS. 21A, 21B, 22A and 22B can also be set such that the balloon 653 is given an apple-shaped cross section.

When the balloon 703 of the retractor according to the preferred embodiment of the invention is deployed inside an organ, and the hollow shaft 701 is manipulated, the tether 711 limits the maximum distance of the distal tip 707 of the balloon from the distal end 705 of the hollow shaft to a distance corresponding to the length of the balloon in its unstressed expanded state.

A manipulation force applied proximally in the direction of the axis of the hollow shaft 701 causes some balloon distention, but the amount of distention is substantially reduced by applying the manipulation force to the balloon at two points, i.e., at the connection between the balloon 703 and the tether 711 and at the connection between the balloon and the distal end 705 of the hollow shaft. Any distal excursion of the distal tip 707 of the elastomeric balloon in response to a manipulation force in the proximal direction is limited by the tether. Limiting distal excursion of the distal tip of the elastomeric balloon further reduces distention. On the other hand, the tether, being free to slide proximally through the tether anchor 704, allows the distal tip of the elastomeric balloon to move freely in the proximal direction in response to a manipulation force in the distal direction. The tether thus has no ability to puncture or otherwise injure the organ when a manipulation force is applied in the distal direction.

The distal tip 707 of the balloon has some freedom of movement in directions perpendicular to the axis of the hollow shaft 701. However, the freedom of movement in these directions is restricted by the tether 711 contacting the distal end 705 of the hollow shaft. When the tether contacts the distal end of the hollow shaft, the tether cannot move further, whereupon the tether increases the stiffness of the balloon in the direction perpendicular to the axis of the hollow shaft.

Although the tether is free to slide relative to the hollow shaft, it is not free to rotate. This enables the surgeon to rotate the organ by applying a torque about the axis of the hollow shaft. With a rotationally fixed tether, the manipulating torque is transferred to the balloon, and hence to the organ, by both the connection between the balloon and the tether and the connection between the balloon and the hollow shaft. Sharing the manipulating torque between two points reduces the peak stress in the balloon, and significantly reduces twisting in the balloon. This provides the surgeon with greater control and reduces the risk of the balloon rupturing.

Although the foregoing invention has been described in detail for purposes of clarity of understanding, it will be obvious that certain modifications may be practiced within the scope of the appended claims.

We claim:

1. An apparatus for applying a manipulating force to manipulate a hollow body, the apparatus comprising:
   a hollow shaft having a distal end;
   a first hollow tube having a distal end, being coaxially mounted outside the hollow shaft, and being axially fixed relative to the hollow shaft;
   a second hollow tube having a distal end providing a cutting edge, the second hollow tube being coaxially mounted between the hollow shaft and the first hollow tube, and being axially slidable relative to the hollow shaft and the first hollow tube;
   an elastomeric balloon attached to the distal end of the hollow shaft, the elastomeric balloon having a distal tip, and being inflatable from a collapsed state to an expanded state to engage the hollow body; and
   a tethering means, attached to the distal tip of the elastomeric balloon, for limiting distal excursion and freely permitting proximal excursion of the distal tip of the elastomeric balloon in the expanded state in response to the manipulating force.

2. The apparatus of claim 1, wherein
   the tethering means is flexible and includes a distal end and a proximal end,
   the distal end is attached to the distal tip of the elastomeric balloon, and
   the proximal end is attached within the hollow shaft.

3. The apparatus of claim 2, wherein the second hollow tube includes a shoulder means, proximate to the distal end, for restricting penetration of the distal end into the hollow body.

4. The apparatus of claim 1, wherein the second hollow tube includes a shoulder means, proximate to the distal end, for restricting penetration of the distal end into the hollow body.

5. An apparatus for applying a manipulating force to manipulate a hollow body, the apparatus comprising:
   a hollow shaft having a distal end;
   an elastomeric balloon attached to the distal end of the hollow shaft, the elastomeric balloon having a distal tip, and being inflatable from a collapsed state to an expanded state to engage the hollow body; and
   a tethering means, attached to the distal tip of the elastomeric balloon, for limiting distal excursion and freely permitting proximal excursion of the distal tip of the elastomeric balloon in the expanded state in response to the manipulating force, the tethering means comprising:
      a rigid elongate member slidably mounted within the hollow shaft, the elongate member having a proximal end, and a distal end, the distal tip of the balloon is attached to the distal end of the elongate member, and
      a stop means for limiting distal sliding of the elongate member.

6. The apparatus of claim 5, wherein the apparatus additionally comprises a keying means for transferring a torque from the hollow shaft to the distal tip of the balloon via the elongate member.

7. The apparatus of claim 6, wherein
   the hollow shaft includes a portion of reduced cross sectional area, the portion of reduced cross-sectional area including a first flat,
   the elongate member includes a second portion of reduced cross-sectional area, the second portion of reduced cross-sectional area being elongate, sliding within the first portion of reduced cross-sectional area, and including a second flat engaging with the first flat, and the first flat and the second flat together provide the keying means.

8. The apparatus of claim 5, wherein the hollow shaft includes a first portion of reduced cross-sectional area, the elongate member includes a second portion of reduced cross-sectional area, the second portion of reduced cross-sectional area being elongate, sliding within the first portion of reduced cross-sectional area, and including a proximal end, a distal end, and a shoulder at the proximal end, and the first portion of reduced cross sectional area and the shoulder together provide the stop means.

9. The apparatus of claim 8, wherein the apparatus additionally comprises a keying means for transferring a torque from the hollow shaft to the distal tip of the balloon via the elongate member.

10. The apparatus of claim 9, wherein the first portion of reduced cross-sectional area includes a first flat, the second portion of reduced cross-sectional area includes a second flat engaging with the first flat, and the first flat and the second flat together provide the keying means.

11. The apparatus of claim 5, wherein the elongate member comprises a shaft having a distal end and a proximal end, and a collar at the proximal end, the apparatus additionally includes a tether anchor attached within the hollow shaft, the shaft being slidably mounted in the tether anchor, and the collar and the tether anchor together provide the stop means.

12. The apparatus of claim 5, wherein the distal end of the elongate member includes an axial bore, the axial bore receives the distal tip of the elastomeric balloon and a rigid object adapted for fitting in the axial bore, and the distal tip of the balloon and the rigid object are constrained within the axial bore by crimping.

13. The apparatus of claim 5, wherein the apparatus additionally comprises:

a first hollow tube having a distal end, being coaxially mounted outside the hollow shaft, and being axially fixed relative to the hollow shaft, and a second hollow tube having a distal end providing a cutting edge, the second hollow tube being coaxially mounted between the hollow shaft and the first hollow tube, and being axially slidable relative to the hollow shaft and the first hollow tube.

14. The apparatus of claim 13, wherein the second hollow tube includes a shoulder means, proximate to the distal end, for restricting penetration of the distal end into the hollow body.

15. A method of applying a manipulating force to manipulate a hollow body, the method comprising the steps of:

providing a retractor, comprising:

a hollow shaft having a distal end;

an elastomeric balloon attached to the distal end of the hollow shaft, the elastomeric balloon having a distal tip, and being inflatable from a collapsed state to an expanded state to engage the hollow body; and a tethering means, attached to the distal tip of the elastomeric balloon, for limiting distal excursion and freely permitting proximal excursion of the distal tip of the elastomeric balloon in the expanded state in response to the manipulating force, the tethering means comprising:

a rigid elongate member slidably mounted within the hollow shaft, the elongate member having a proximate end and a distal end, the distal tip of the balloon being attached to the distal end of the elongate member, and a stop means for limiting distal sliding of the elongate member, introducing the elastomeric balloon in the collapsed state into an interior volume of the hollow body, expanding the elastomeric balloon to the expanded state to occupy at least a major portion of the interior volume, and applying the manipulating force to the hollow shaft to manipulate the hollow body.

16. The method of claim 15, additionally for dissecting the hollow body, wherein the step of applying the manipulating force to the hollow shaft includes the step of separating attachment of the hollow body from surrounding tissues while simultaneously manipulating the hollow shaft to reposition the hollow body.

17. The method of claim 15, wherein, in the step of providing a retractor, the retractor additionally comprises a keying means for transferring a torque from the hollow shaft to the distal tip of the balloon via the elongate member.

18. The method of claim 17, wherein, in the step of providing a retractor:

the hollow shaft includes a portion of reduced cross sectional area, the portion of reduced cross-sectional area including a first flat;

the elongate member includes a second portion of reduced cross-sectional area, the second portion of reduced cross-sectional area being elongate, sliding within the first portion of reduced cross-sectional area, and including a second flat engaging with the first flat; and the first flat and the second flat together provide the keying means.

19. The method of claim 15, wherein, in the step of providing a retractor:

the hollow shaft includes a first portion of reduced cross-sectional area, the elongate member includes a second portion of reduced cross-sectional area, the second portion of reduced cross-sectional area being elongate, sliding within the first portion of reduced cross-sectional area; and including a proximal end, a distal end, and a shoulder at the proximal end; and the first portion of reduced cross sectional area and the shoulder together provide the stop means.

20. The method of claim 19, wherein, in the step of providing a retractor, the retractor additionally comprises a keying means for transferring a torque from the hollow shaft to the distal tip of the balloon via the elongate member.

21. The method of claim 20, wherein, in the step of providing a retractor:

the first portion of reduced cross-sectional area includes a first flat;

the second portion of reduced cross-sectional area includes a second flat engaging with the first flat; and the first flat and the second flat together provide the keying means.

22. The method of claim 15, wherein, in the step of providing a retractor:
   the elongate member comprises a shaft having a distal end and a proximal end, and a collar at the proximal end;
   the retractor additionally includes a tether anchor attached within the hollow shaft, the shaft being slidably mounted in the tether anchor, and
   the collar and the tether anchor together provide the stop means.

23. The method of claim 15, wherein, in the step of providing a retractor:
   the distal end of the elongate member includes an axial bore;
   the axial bore receives the distal tip of the elastomeric balloon and a rigid object adapted for fitting in the axial bore; and
   the distal tip of the balloon and the rigid object are constrained within the axial bore by crimping.

24. The method of claim 15, wherein, in the step of providing a retractor, the retractor additionally comprises:
   a first hollow tube having a distal end, being coaxially mounted outside the hollow shaft, and being axially fixed relative to the hollow shaft; and
   a second hollow tube having a distal end providing a cutting edge, the second hollow tube being coaxially mounted between the hollow shaft and the first hollow tube, and being axially slidable relative to the hollow shaft and the first hollow tube.

25. The method of claim 24, wherein, in the step of providing a retractor, the second hollow tube includes a shoulder means, proximate to the distal end, for restricting penetration of the distal end into the hollow body.

* * * * *